United States Patent [19]

Lesieur et al.

[11] Patent Number: 6,147,110

[45] Date of Patent: Nov. 14, 2000

[54] HETEROCYCLIC COMPOUNDS

[75] Inventors: Daniel Lesieur, Gondecourt; Nicolas Ruiz, Paris; Valérie Wallez, Wervicq-Sud; Sophie Boye, Vincennes; Caroline Bennejean, Charenton Le Pont; Pierre Renard, Le Chesnay; Philippe Delagrange, Issy Les Moulineaux, all of France

[73] Assignee: Adir et Compagnie, Courbevoie, France

[21] Appl. No.: 09/219,981

[22] Filed: Dec. 23, 1998

[30] Foreign Application Priority Data

Dec. 24, 1997 [FR] France .................... 97 16468

[51] Int. Cl.[7] .......................... A61K 31/34; A61K 31/44; A61K 31/38

[52] U.S. Cl. .......................... 514/470; 514/337; 514/443; 514/444; 514/469; 546/280.4; 546/284.1; 549/50; 549/58; 549/60; 549/469

[58] Field of Search .................... 549/50, 469, 470, 549/60, 58; 514/443, 469, 444, 337; 546/280.4, 284.1

*Primary Examiner*—Amelia Owens
*Attorney, Agent, or Firm*—The Firm of Gordon W. Hueschen

[57] ABSTRACT

Compound of formula (I):

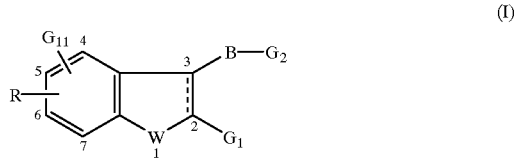

wherein:

B represents optionally substituted $(C_1-C_6)$-alkylene,

W represents oxygen or sulphur,

R represents hydrogen, hydroxy, R', or OR', R' being as defined in the description, $G_1$ and $G_{11}$ are as defined in the description, $G_2$ represents a group selected from:

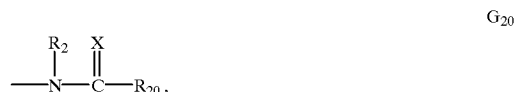

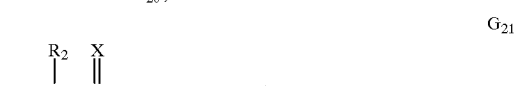

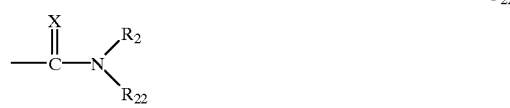

wherein $R_{20}$, $R_{21}$, and $R_2$ are as defined in the description, and medicinal products containing the same which are useful as melatoninergic ligands.

23 Claims, No Drawings

HETEROCYCLIC COMPOUNDS

DESCRIPTION OF THE PRIOR ART

Patent Applications EP 721 938 and EP 721 947 describe heterocyclic compounds of the arylalkylamide and arylalkylurea type that are melatonin receptor ligands. Those compounds are characterised by the presence of a single substituent on the ring structure carrying the alkylamide chain. In Patent Specification EP 527 687 compounds having a similar structure were studied for their action in respect of the melatoninergic system. Those compounds are characterised by the presence of a N-cycloalkylamidoalkyl chain grafted onto a benzo[b]thiophene or benzo[b]furan ring structure. Such heterocycles are also described in the Applications EP 745 583 and WO 97 06140 as melatoninergic ligands and are characterised by the presence of a substituent of the acyl or alkyl type in selected positions of the heterocyclic ring structure.

BACKGROUND OF THE INVENTION

Numerous studies in the last ten years have demonstrated the key role of melatonin (N-acetyl-5-methoxytryptamine) in many physiopathological phenomena and in the control of circadian rhythm. Its half-life is quite short, however, owing to the fact that it is rapidly metabolised. Great interest therefore lies in the possibility of providing the clinician with melatonin analogues that are metabolically more stable, have an agonist or antagonist character and may be expected to have a therapeutic effect that is superior to that of the hormone itself.

In addition to their beneficial action on circadian rhythm disorders (J. Neurosurg. 1985, 63, pp. 321–341) and sleep disorders (Psychopharmacology, 1990, 100, pp. 222–226), ligands of the melatoninergic system have valuable pharmacological properties in respect of the central nervous system, especially anxiolytic and antipsychotic properties (Neuropharmacology of Pineal Secretions, 1990, 8 (3–4), pp. 264–272) and analgesic properties (Pharmacopsychiat., 1987, 20, pp. 222–223), as well as for the treatment of Parkinson's disease (J. Neurosurg. 1985, 63, pp. 321–341) and Alzheimer's disease (Brain Research, 1990, 528, pp. 170–174). Those compounds have also demonstrated activity in relation to certain cancers (Melatonin—Clinical Perspectives, Oxford University Press, 1988, pp. 164–165), ovulation (Science 1987, 227, pp. 714–720), diabetes (Clinical Endocrinology, 1986, 24, pp. 359–364), and in the treatment of obesity (International Journal of Eating Disorders, 1996, 20(4), pp. 443–446).

Those various effects are exerted via the intermediary of specific melatonin receptors. Molecular biology studies have demonstrated the existence of a number of receptor sub-types that are capable of binding that hormone (Trends Pharmacol. Sci., 1995, 16, p. 50; WO 97,04094). It has been possible, for various species, including mammals, for some of those receptors to be located and characterised. In order to be able to understand the physiological functions of those receptors better, it is of great advantage to have available specific ligands. Moreover such compounds, by interacting selectively with one or other of those receptors, may be excellent medicaments for the clinician in the treatment of pathologies associated with the melatoninergic system, some of which have been mentioned above.

The compounds of the present invention have a novel structure characterised by a heterocyclic ring structure that is substituted by an alkylamide chain and that in addition has two substituents on the main ring structure. Surprisingly, that structure confers on them a very high affinity for melatonin receptors and a selectivity for one or other of the receptor sub-types.

DETAILED DESCRIPTION OF THE INVENTION

The invention relates to compounds of formula (I):

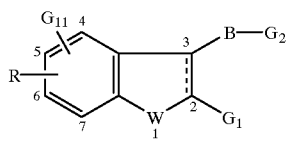

wherein:

the 2–3 bond is saturated or unsaturated

W represents an oxygen atom or a sulphur atom,

B represents a linear or branched $(C_1-C_6)$-alkylene chain optionally substituted by one or more linear or branched $(C_1-C_6)$-alkyl, hydroxy, linear or branched $(C_1-C_6)$-alkoxy, carboxy and/or linear or branched $(C_1-C_6)$-alkoxycarbonyl groups, R represents a hydrogen atom, a hydroxy group, a radical R' or a group OR', R' representing an optionally substituted linear or branched $(C_1-C_6)$-alkyl group, an optionally substituted linear or branched $(C_2-C_6)$-alkenyl group, an optionally substituted linear or branched $(C_2-C_6)$-alkynyl group, an optionally substituted $(C_3-C_7)$-cycloalkyl group, a linear or branched $(C_1-C_6)$-trihaloalkylsulphonyl group, an optionally substituted aryl group, an optionally substituted biphenyl group or an optionally substituted heteroaryl group, $G_1$ represents a halogen atom, a linear or branched $(C_1-C_6)$-trihaloalkylsulphonyloxy group, a carboxy, formyl or cyano group, a radical $R_1$, or a group —CO—$R_1$ or —O—CO—$R_1$, $R_1$ representing an optionally substituted linear or branched $(C_1-C_6)$-alkyl group, an optionally substituted linear or branched $(C_2-C_6)$-alkenyl group, an optionally substituted linear or branched $(C_2-C_6)$-alkynyl group, an optionally substituted $(C_3-C_7)$-cycloalkyl group, an optionally substituted aryl group, an optionally substituted biphenyl group or an optionally substituted heteroaryl group, in which case $G_{11}$ represents a hydrogen atom or $G_{11}$ and R form together with the carbon atoms carrying them a ring having from 5 to 7 members that is saturated or unsaturated and contains an oxygen atom, that ring optionally being substituted by one or more groups selected from linear or branched $(C_1-C_6)$-alkyl, linear or branched $(C_1-C_6)$-alkoxy, hydroxy, oxo, carboxy and linear or branched $(C_1-C_6)$-alkoxycarbonyl, $G_1$ represents a hydrogen atom, in which case $G_{11}$ represents a linear or branched $(C_1-C_6)$-trihaloalkylsulphonyloxy group, a carboxy, formyl or cyano group, a radical $R_1$, or a group —CO—$R_1$ or —O—CO—$R_1$, $R_1$ representing an optionally substituted linear or branched $(C_1-C_6)$-alkyl group, an optionally substituted linear or branched $(C_2-C_6)$-alkenyl group, an optionally substituted linear or branched $(C_2-C_6)$-alkynyl group, an optionally substituted $(C_3-C_7)$-cycloalkyl group, an optionally substituted aryl group, an optionally substituted biphenyl group or an optionally substituted heteroaryl group.

$G_2$ represents a group selected from:

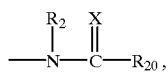
(G20)

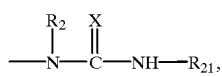
(G21)

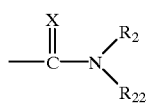
(G22)

wherein:

X represents an oxygen atom or a sulphur atom, $R_2$ represents a hydrogen atom or a linear or branched ($C_1$–$C_6$)-alkyl group, $R_{20}$, $R_{21}$ and $R_{22}$ each represents an optionally substituted linear or branched ($C_1$–$C_6$)-alkyl group, an optionally substituted linear or branched ($C_2$–$C_6$)-alkenyl group, an optionally substituted linear or branched ($C_2$–$C_6$)-alkynyl group, an optionally substituted ($C_3$–$C_7$)-cycloalkyl group, an optionally substituted heteroaryl group, an optionally substituted aryl group or an optionally substituted biphenyl group, provided that:

when $G_2$ represents a group $G_{22}$ wherein $R_{22}$ as defined above is other than an optionally substituted aryl, optionally substituted heteroaryl or optionally substituted biphenyl group, then $G_1$ or $G_{11}$ represents a heteroaryl group (other than pyridyl) that is optionally substituted, a linear or branched ($C_1$–$C_6$)-alkyl group substituted by a heteroaryl group (other than pyridyl) that is optionally substituted, or a group —CO—$R_1$ or O—CO—$R_1$, $R_1$ being as defined above, when $G_2$ represents a group $G_{20}$ or $G_{21}$ wherein $R_{20}$ and $R_{21}$ are other than an optionally substituted aryl, optionally substituted biphenyl or optionally substituted heteroaryl group, and $G_1$ is other than an optionally substituted heteroaryl or optionally substituted naphthyl group, or $G_{11}$ is other than an optionally substituted heteroaryl or optionally substituted naphthyl group while R represents a hydrogen atom, then B represents an optionally substituted methylene or ethylene chain, when $G_2$ represents a group $G_{20}$ or $G_{21}$, or $R_{20}$ or $R_{21}$ as defined above being other than an optionally substituted aryl group or an optionally substituted heteroaryl group and:

when R and $G_1$ each represents a hydrogen atom, then $G_{11}$ is other than a linear or branched ($C_1$–$C_6$)-alkyl group, other than a ($C_3$–$C_7$)-cycloalkyl group optionally substituted by one or more halogen atoms or hydroxy groups, and other than a linear or branched ($C_1$–$C_6$)-alkyl group substituted by one or more halogen atoms or hydroxy or linear or branched ($C_1$–$C_6$)-alkoxy groups, or ($C_3$–$C_7$)-cycloalkyl groups optionally substituted by one or more halogen atoms or hydroxy groups, when $G_1$ represents a hydrogen atom and R represents a group OR', R' as defined above being other than an optionally substituted heteroaryl group, then $G_{11}$ is other than a linear or branched ($C_1$–$C_6$)-alkyl group, a linear or branched ($C_2$–$C_6$)-alkenyl group or a linear or branched ($C_2$–$C_6$)-alkynyl group, when $G_2$ represents either a group $G_{21}$, wherein $R_{21}$ is other than an optionally substituted linear or branched ($C_2$–$C_6$)-alkenyl group and other than an optionally substituted ($C_2$–$C_6$)-alkynyl group, or a group $G_{20}$, wherein $R_{20}$ represents a ($C_3$–$C_7$)-cycloalkyl group optionally substituted by one or more halogen atoms or hydroxy or linear or branched ($C_1$–$C_6$)-alkoxy groups, or a linear or branched ($C_1$–$C_6$)-alkyl group substituted by a ($C_3$–$C_7$)-cycloalkyl group optionally substituted by one or more halogen atoms or hydroxy or linear or branched ($C_1$–$C_6$)-alkoxy groups, then:

$G_{11}$ is other than a linear or branched ($C_1$–$C_6$)-alkyl group, $G_1$ is other than a halogen atom, a linear or branched ($C_1$–$C_6$)-alkyl group, a linear or branched ($C_1$–$C_6$)-alkyl group substituted by an optionally substituted phenyl group, and other than an optionally substituted phenyl group, when $G_2$ represents a group $G_{21}$, X representing a sulphur atom and B an ethylene chain, then $R_{21}$ is other than an optionally substituted aryl group, the term "aryl" denoting a phenyl or naphthyl group, the term "heteroaryl" denoting a saturated or unsaturated, 4- to 11-membered, mono- or bi-cyclic group containing from 1 to 4 hetero atoms selected from nitrogen, oxygen and sulphur, for example furyl, pyridyl, thienyl, . . .

it being understood that:

the expression "optionally substituted" applied to the terms "alkyl", "alkenyl", "alkynyl" and "cycloalkyl" means that those groups are, if desired, substituted by one or more halogen atoms and/or ($C_3$–$C_7$)-cycloalkyl, hydroxy, linear or branched ($C_1$–$C_6$)-alkoxy, optionally substituted aryl and/or optionally substituted heteroaryl groups, the expression "optionally substituted" applied to the terms "aryl", "biphenyl" and "heteroaryl" means that those groups are, if desired, substituted by one or more halogen atoms and/or linear or branched ($C_1$–$C_6$)-alkyl groups, linear or branched ($C_1$–$C_6$)-trihaloalkyl groups, hydroxy groups, linear or branched ($C_1$–$C_6$)-alkoxy groups, nitro groups, amino groups (optionally substituted by one or two identical or different, linear or branched ($C_1$–$C_6$)-alkyl groups), linear or branched ($C_1$–$C_6$)-alkylcarbonyl groups, cyano groups, carboxy groups, and/or aminocarbonyl groups (optionally substituted by one or two identical or different, linear or branched ($C_1$–$C_6$)-alkyl groups), their enantiomers and diastereoisomers, and also addition salts thereof with a pharmaceutically acceptable acid or base.

Amongst the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid, etc..

Amongst the pharmaceutically acceptable bases there may be mentioned by way of non-limiting example sodium hydroxide, potassium hydroxide, triethylamine, tert-butylamine, etc..

The invention relates preferably to benzo[b]furan or benzo[b]thiophene compounds.

In the compounds of formula (I), preferably B represents a linear or branched ($C_1$–$C_6$)-alkylene chain, more especially an ethylene chain.

Preferred compounds of the invention are those wherein $G_{11}$ represents a hydrogen atom.

Other preferred compounds of the invention are those wherein $G_1$ and R each represents a hydrogen atom.

The group R present in the compounds of formula (I) is preferably attached in the 5-position of the heterocyclic ring structure.

The group $G_{11}$ present in the compounds of formula (I) is preferably attached in the 5-position of the heterocyclic ring structure.

Preferred groups R of the invention are selected from hydrogen and the radicals R' and OR' wherein R' represents a linear or branched $(C_1-C_6)$-alkyl group, a linear or branched $(C_2-C_6)$-alkenyl group or a linear or branched $(C_2-C_6)$-alkynyl group. More especially, R' represents a linear or branched $(C_1-C_6)$-alkyl group, for example a methyl or ethyl group.

An advantageous embodiment of the invention concerns compounds of formula (I) wherein $G_1$ represents an optionally substituted aryl group, an optionally substituted heteroaryl group, or a linear or branched $(C_1-C_6)$-alkyl group substituted by a group selected from $(C_3-C_7)$-cycloalkyl, optionally substituted aryl and optionally substituted heteroaryl. More especially, $G_1$ represents a methylene group substituted by an optionally substituted phenyl group.

Another advantageous embodiment of the invention concerns compounds of formula (I) wherein $G_{11}$ represents an optionally substituted aryl group, an optionally substituted heteroaryl group, or a linear or branched $(C_1-C_6)$-alkyl group substituted by a group selected from $(C_3-C_7)$-cycloalkyl, optionally substituted aryl and optionally substituted heteroaryl, while $G_1$ represents a hydrogen atom.

In the preferred groups $G_2$ of the invention, X represents an oxygen atom, $R_2$ represents a hydrogen atom and $R_{20}$, $R_{21}$ and $R_{22}$ are selected from the groups linear or branched $(C_2-C_6)$-alkenyl, and linear or branched $(C_1-C_6)$-alkyl optionally substituted by one or more halogen atoms. Preferably, $G_2$ represents a group $G_{20}$.

A very advantageous embodiment of the invention concerns compounds of formula (I) wherein the 2–3 bond is unsaturated, B represents an ethylene chain, R, attached in the 5-position of the heterocyclic ring structure, represents a hydrogen atom or a group R' or OR' wherein R' is a linear or branched $(C_1-C_6)$-alkyl group, $G_{11}$ represents a hydrogen atom, $G_1$ represents an optionally substituted aryl group, an optionally substituted heteroaryl group, or a linear or branched $(C_1-C_6)$-alkyl group substituted by a $(C_3-C_7)$-cycloalkyl group, by an optionally substituted aryl group or by an optionally substituted heteroaryl group, and $G_2$ represents a group $G_{20}$ wherein X represents an oxygen atom, $R_2$ represents a hydrogen atom and $R_{20}$ represents a linear or branched $(C_2-C_6)$-alkenyl group, or a linear or branched $(C_1-C_6)$-alkyl group optionally substituted by one or more halogen atoms.

Another very advantageous embodiment of the invention concerns compounds of formula (I) wherein the 2–3 bond is unsaturated, B represents an ethylene chain, R and $G_1$ each represents a hydrogen atom, $G_{11}$, attached in the 5-position of the heterocyclic ring structure, represents an optionally substituted aryl group, an optionally substituted heteroaryl group, or a linear or branched $(C_1-C_6)$-alkyl group substituted by an optionally substituted aryl group or by an optionally substituted heteroaryl group, and $G_2$ represents a group $G_{20}$ wherein X represents an oxygen atom, $R_2$ represents a hydrogen atom and $R_{20}$ represents a linear or branched $(C_2-C_6)$-alkenyl group, or a linear or branched $(C_1-C_6)$-alkyl group optionally substituted by one or more halogen atoms.

Among the preferred compounds of the invention there may be mentioned more especially:

N-{2-[5-methoxy-2-(3-methoxybenzyl)-3-benzo[b]furyl]ethyl}acetamide

N-{2-[5-methoxy-2-(3-trifluoromethylbenzyl)-3-benzo[b]furyl]ethyl}acetamide

N-[2-(2-benzyl-5-methoxy-3-benzo[b]furyl]ethyl}acrylamide

N-{2-[5-(2-methoxyphenyl)-3-benzo[b]furyl]ethyl}acetamide

The invention relates also to a process for the preparation of compounds of formula (I) which is characterised in that there is used as starting material a compound of formula (II):

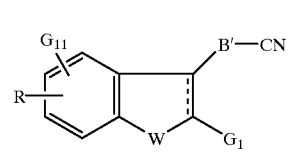

(II)

wherein R, W, $G_1$ and $G_{11}$ are as defined for formula (I) and B' represents a linear or branched $(C_0-C_5)$-alkylene chain optionally substituted by one or more linear or branched $(C_1-C_6)$-alkyl, hydroxy, linear or branched $(C_1-C_6)$-alkoxy, carboxy and/or linear or branched $(C_1-C_6)$-alkoxycarbonyl groups, which is subjected either to a reduction reaction, which may be a catalytic hydrogenation or a chemical reduction (for example using the complex borane-tetrahydrofuran), to yield a compound of formula (III):

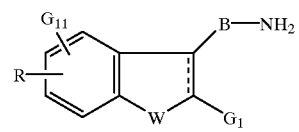

(III)

wherein R, W, $G_1$ and $G_{11}$ are as defined hereinbefore and B is as defined for formula (I), a) which may be subjected to the action of an acyl chloride of formula (IV)

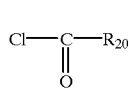

(IV)

wherein $R_{20}$ is as defined for formula (I),
to yield a compound of formula (I/a):

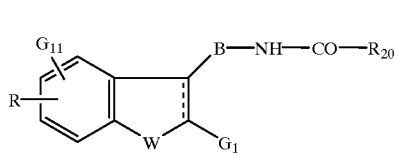

(I/a)

a particular case of the compounds of formula (I) wherein R, W, B, $G_1$, $G_{11}$ and $R_{20}$ are as defined hereinbefore,
which compound I/a may, if desired, be subjected to a conventional alkylation reaction using as reagent a compound of formula P—R'$_2$ wherein P represents a leaving group (such as a halogen or a tosyl group) and R'$_2$, which is other than a hydrogen atom, has the same meaning as R$_2$ in formula (I), or using a dialkyl sulphate, to yield a compound of formula (I/b):

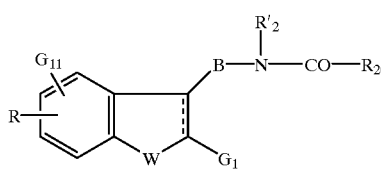
(I/b)

a particular case of the compounds of formula (I) wherein R, W, B, G$_1$, G$_{11}$, R'$_2$ and R$_{20}$ are as defined hereinbefore, which compounds (I/a) and (I/b) may be subjected to the action of a thionisation agent, for example Lawesson's reagent, to obtain a compound of formula (I/c):

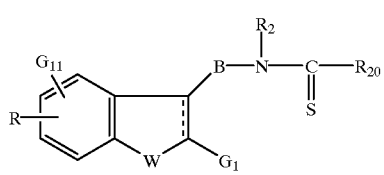
(I/c)

a particular case of the compounds of formula (I) wherein R, W, B, G$_1$, G$_{11}$, R$_2$ and R$_{20}$ are as defined hereinbefore, b) or which may be subjected to the action of an iso(thio)cyanate of formula (V):

X=C=N—R$_{21}$ (V)

wherein X and R$_{21}$ are as defined for formula (I), to yield a compound of formula (I/d):

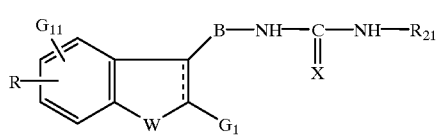
(I/d)

a particular case of the compounds of formula (I) wherein R, W, B, G$_1$, G$_{11}$, X and R$_{21}$ are as defined hereinbefore, which compound (I/d) may be subjected to an alkylation reaction using a conventional alkylation agent of formula P—R'$_2$ wherein P is a leaving group (for example a halogen atom or a tosyl group) and R'$_2$, which is other than a hydrogen atom, has the same meaning as R$_2$ in formula (I), or using a dialkyl sulphate, to yield a compound of formula (I/e):

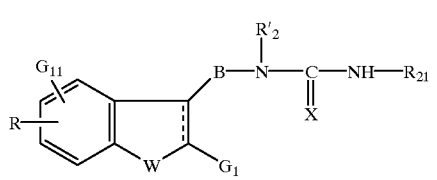
(I/e)

a particular case of the compounds of formula (I) wherein R, W, B, G$_1$, G$_{11}$, R'$_2$, X and R$_{21}$ are as defined hereinbefore, or to a hydrolysis reaction in acid or basic medium to yield the corresponding carboxylic acid of formula (VI):

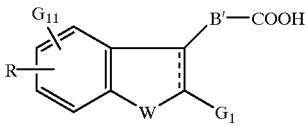
(VI)

wherein R, W, G$_1$ and G$_{11}$ are as defined for formula (I), and B' is as defined hereinbefore, which is reacted after optional formation of the corresponding acid chloride, with a compound of formula (VII):

(VII)

wherein R$_2$ and R$_{22}$ are as defined for formula (I), to yield a compound of formula (I/f):

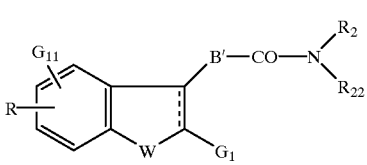
(I/f)

a particular case of the compounds of formula (I) wherein R, W, B', G$_1$, G$_{11}$, R$_2$ and R$_{22}$ are as defined hereinbefore, which compound of formula (I/f) may, if desired, be subjected to the action of a thionisation agent, for example Lawesson's reagent, to yield a compound of formula (I/g):

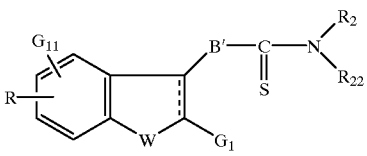
(I/g)

a particular case of the compounds of formula (I) wherein R, W, B', G$_1$, G$_{11}$, R$_2$ and R$_{22}$ are as defined hereinbefore, which compounds of formula (I/a), (I/b), (I/c), (I/d), (I/e), (I/f) and (I/g), when R represents a group O-Alk (-Alk representing a linear or branched (C$_1$–C$_6$)-alkyl group) and G$_{11}$ represents a group G'$_{11}$ that is not capable of forming a ring with R, may, when that is compatible with the substituents present in the molecule, be treated with boron tribromide to yield the corresponding hydroxylated compound of formula (VIII):

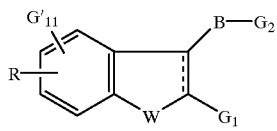

(VIII)

wherein W, $G_1$, B and $G_2$ are as defined for formula (I) and $G'_{11}$ has the same meaning as $G_{11}$ in formula (I), the hydroxylated function of which compound of formula (VIII) may be:

a) converted into trifluoromethanesulphonate using, for example, phenyl bis(trifluoromethanesulphonimide) in basic medium, to yield a compound of formula (IX):

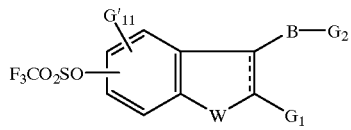

(IX)

wherein W, $G_1$, $G'_{11}$, B and $G_2$ are as defined hereinbefore, which may be converted, by way of a reaction catalysed by a palladium(0) compound using as reagent a boric acid compound R'B(OH)$_2$ or a tin compound (R'SnBu$_3$) wherein R' is as defined for formula (I), to obtain a compound of formula (I/h):

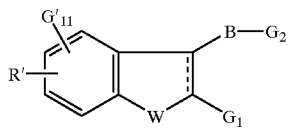

(I/h)

a particular case of the compounds of formula (I) wherein R', W, $G_1$, $G'_{11}$, B and $G_2$ are as defined hereinbefore, b) subjected to an O-substitution reaction in basic medium, using as reagent the appropriate halogenated compound, to yield a compound of formula (I/i):

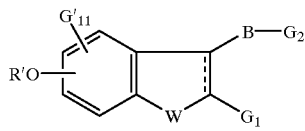

(I/i)

a particular case of the compounds of formula (I) wherein R', W, $G_1$, $G'_{11}$, B and $G_2$ are as defined hereinbefore, or, c) when $G'_{11}$ represents a hydrogen atom, subjected to an O-substitution reaction to yield a compound of formula (X):

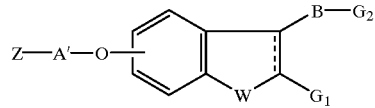

(X)

wherein W, $G_1$, $G_2$ and B are as defined hereinbefore, A' represents a $(C_1$–$C_3)$-alkylene, $(C_2$–$C_3)$-alkenylene or $(C_2$–$C_3)$-alkynylene chain, and Z represents a reactive function (for example a carboxylic acid or an ester) or forms with A' a double or triple bond, which may be cyclised, by way of an intramolecular electrophilic substitution reaction when Z represents a reactive function or by way of a Claisen rearrangement when Z forms with A' a double or triple bond, to yield a compound of formula (I/k):

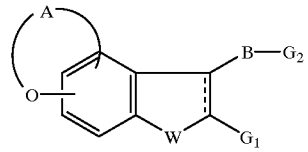

(I/k)

a particular case of the compounds of formula (I) wherein W, $G_1$, $G_2$, and B are as defined hereinbefore and A represents a $(C_2$–$C_4)$-alkylene, $(C_3$–$C_4)$-alkenylene or $(C_3$–$C_4)$-alkynylene chain, or a $(C_2$–$C_4)$-alkylene chain substituted by an oxo group, it being possible for the latter to be converted, if desired, into a hydroxy, linear or branched $(C_1$–$C_6)$-alkoxy or linear or branched $(C_1$–$C_6)$-alkyl group, which compounds (I/a) to (I/k) and (IX), constituting the totality of the compounds of formula (I), are, if necessary, purified according to a conventional purification technique, are, where appropriate, separated into their enantiomers according to a conventional separation technique, and are, if desired, converted into their addition salts with a pharmaceutically acceptable acid or base.

When it is useful for the purpose of simplifying the above process, one of the groups $G_1$ and $G_{11}$ as defined formula (I) may be converted into another group represented in the description of $G_1$ or of $G_{11}$ in formula (I) employing the conventional reactions of organic chemistry.

The starting materials used in the process described above are either commercial products or are products readily obtainable by the person skilled in the art according to processes well known in the literature.

For example, the compounds of formula (II) as defined hereinbefore may be obtained starting from the corresponding carbonyl compound of formula (XI):

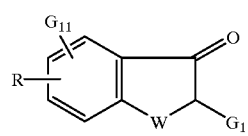

(XI)

wherein R, W, $G_1$ and $G_{11}$ are as defined for formula (I), by a Wittig, Horner Emmons or Knoevenagel reaction, according to the reagents available.

When it may prove advantageous, a compound of formula (VI/a):

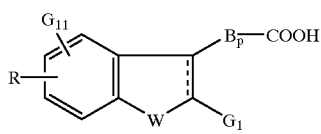

(VI/a)

a particular case of the compounds of formula (VI) wherein R, W, $G_1$ and $G_{11}$ are as defined for formula (I) and $B_p$ represents a chain carrying p carbon atoms as defined for B in formula (I), p being an integer of from 0 to 5, may be subjected to a sequence of reactions with the aim of homologizing the carbon chain carrying the acid function, that sequence of reactions comprising reduction of the acid to alcohol, conversion of the hydroxy into a leaving group, and substitution of that group by a cyano compound to yield a compound of formula (II/a):

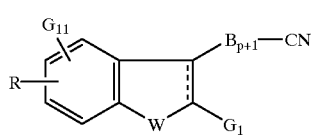

(II/a)

a particular case of the compounds of formula (II) wherein R, W, $G_1$, $G_{11}$ and $B_p$ are as defined hereinbefore.

The compounds of formula (XI) as defined hereinbefore are either known to the person skilled in the art or may be obtained from commercial compounds, or from compounds described in the literature, of formula (XII):

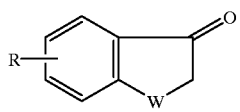

(XII)

wherein R and W are as defined for formula (I),
- either, when $G_{11}$ represents a hydrogen atom, by a condensation reaction of an appropriate aldehyde in basic medium (Tetrahedron lett., 1992, 32, 5937) or by way of an organolithium compound condensed with an appropriate electrophile,
- or, when $G_1$ represents a hydrogen atom, by electrophilic or nucleophilic substitution reactions in various positions of the aromatic ring structure.

The compounds of the invention and the pharmaceutical compositions containing them have proved useful in the treatment of disorders of the melatoninergic system.

Pharmacological study of the compounds of the invention has in fact demonstrated that they are atoxic, have a very high selective affinity for melatonin receptors and have substantial activity on the central nervous system and, in particular, therapeutic properties in respect of sleep disorders, anxiolytic, antipsychotic and analgesic properties, as well as properties in respect of microcirculation have been found, enabling it to be established that the compounds of the invention are useful in the treatment of stress, sleep disorders, anxiety, seasonal affective disorders, cardiovascular pathologies, insomnia and fatigue due to jetlag, schizophrenia, panic attacks, melancholia, appetite disorders, obesity, insomnia, psychotic disorders, epilepsy, diabetes, Parkinson's disease, senile dementia, various disorders associated with normal or pathological ageing, migraine, memory loss, Alzheimer's disease, and in cerebral circulation disorders. In another field of activity, it appears that the compounds of the invention have ovulation-inhibiting and immunomodulating properties and are capable of being used in the treatment of cancers.

The compounds will preferably be used in the treatment of seasonal affective disorders, sleep disorders, cardiovascular pathologies, insomnia and fatigue due to jetlag, appetite disorders and obesity.

For example, the compounds will be used in the treatment of seasonal affective disorders and sleep disorders.

The present invention relates also to pharmaceutical compositions comprising at least one compound of formula (I) on its own or in combination with one or more pharmaceutically acceptable excipients.

Amongst the pharmaceutical compositions according to the invention there may be mentioned more especially those that are suitable for oral, parenteral, nasal, per- or transcutaneous, rectal, perlingual, ocular or respiratory administration, especially tablets or dragées, sublingual tablets, sachets, paquets, gelatin capsules, glossettes, lozenges, suppositories, creams, ointments, dermal gels and drinkable or injectable ampoules.

The dosage varies according to the sex, age and weight of the patient, the route of administration, the nature of the therapeutic indication or any associated treatments, and ranges from 0.01 mg to 1 g per 24 hours in 1 or more administrations.

The following Examples illustrate the invention but do not limit it in any way. The structures of the compounds described have been confirmed by customary spectroscopic techniques.

Preparation A: 2-(5-Methoxy-2-phenyl-3-benzo[b]furyl)acetonitrile

Step a: 5-Methoxy-3-methyl-2phenylbenzo[b]furan

A mixture of 4.5 mmol (1.15 g) of 1-(4-methoxyphenoxy)-1-phenylacetone and 11.5 g of polyphosphoric acid is heated at 50° C. with vigorous stirring for 30 minutes. After cooling, the reaction mixture is slowly poured onto ice and is then extracted with ethyl acetate. The organic phase is subsequently washed with water, dried, concentrated and purified by chromatography on silica gel, using as eluant an 8/2 mixture of petroleum ether/toluene, to yield the expected compound. Melting point: 106–107° C. (ref: J. Chem. Soc. (C), 1970, p. 155)

Step b: 2-(5-Methoxy-2-phenyl-3-benzo[b]furyl)acetonitrile 0.07 mmol (12 mg) of AIBN and 1.46 mmol (0.26 g) of N-bromosuccinimide are added to a solution of 1.46 mmol (0.35 g) of the compound described in the preceding Step in 10 ml of carbon tetrachloride. The reaction mixture is heated at reflux for 15 minutes shielded from light. After cooling, the succinimide formed is filtered off and the filtrate is concentrated. The residue obtained is dissolved in 2 ml of dimethyl sulphoxide and added to a solution of 1.8 mmol (0.08 g) of sodium cyanide in 2 ml of dimethyl sulphoxide. The reaction mixture is heated at 60° C. for 1 hour and is then hydrolysed after cooling. After extraction with ethyl acetate, the organic phase is washed with water, dried, concentrated and purified by chromatography on silica gel, using as eluant an 8/2 mixture of cyclohexane/ethyl acetate, to yield the expected compound. Melting point: 106–107° C.

Preparation B: 2-(2-Benzyl-5-methoxy-3benzo[b]furyl)acetonitrile

Step a: 5-Methoxy-2-(1-phenylmethylidene)-2,3-dihydro-3-benzo[b]furanone 36.5 mmol (3.9 g) of benzaldehyde are added to a solution of 30.5 mmol (5 g) of 5-methoxy-3-benzo[b]furanone in 150 ml of dichloromethane. With vigorous stirring and at ambient temperature, 25 g of basic alumina are then added. Stirring is maintained at ambient temperature for 30 minutes. The mixture is then filtered, the filtrate is concentrated and the residue obtained is washed with a minimum amount of ethanol to yield the expected compound. Melting point: 134° C.

Step b: 2-Benzyl-5-methoxy-2,3-dihydro-3-benzo[b]furanone

A solution of 25.8 mmol (6.5 g) of the compound described in the preceding Step in a mixture of 400 ml of methanol and 100 ml of dioxane is stirred for 1 hour 30 minutes at ambient temperature under hydrogen atmospheric pressure in the presence of 0.65 g of palladium-on-carbon. After filtering off the catalyst, the filtrate is concentrated to yield the expected compound.

Step c: 2-(2-Benzyl-5-methoxy-3-benzo[b]furyl)acetonitrile

Under an inert atmosphere, 38.4 mmol (1.3 g) of 60% sodium hydride in oil are suspended in 80 ml of anhydrous tetrahydrofuran. At a temperature of −10° C., a solution of 38.4 mmol (6.8 g) of diethyl cyanomethylphosphonate in 40 ml of tetrahydrofuran is added dropwise. After 15 minutes' stirring at −10° C., 30 ml of hexamethylphosphoramide, and a solution of 25.6 mmol (6.5 g) of the compound described in the preceding Step in 130 ml of tetrahydrofuran, are added in succession. The reaction mixture is stirred for 2 hours 30 minutes at −10° C. and then hydrolysed. After extraction with ethyl acetate, the combined organic phases are washed with a 1M hydrochloric acid solution and then with a saturated sodium chloride solution. After drying and evaporation of the solvents the residue obtained is purified by chromatography on silica gel, using as eluant a 2/8 mixture of ethyl acetate/petroleum ether, to yield the expected compound. Melting point: 69–70° C.

Preparation C: 2-[5-Methoxy-2-(2-methoxybenzyl)-3-benzo[b]furyl]acetonitrile

The expected product is obtained in accordance with the process described in Preparation B, replacing the benzaldehyde with 2-methoxybenzaldehyde in Step a. Melting point: 122° C.

Preparation D: 2-[5-Methoxy-2-(3-methoxybenzyl)-3-benzo[b]furyl]acetonitrile

The expected product is obtained in accordance with the process described in Preparation B, replacing the benzaldehyde with 3-methoxybenzaldehyde in Step a. Melting point: 81° C.

Preparation E: 2-[5-Methoxy-2-(4-methoxybenzyl)-3-benzo[b]furyl]acetonitrile the expected product is obtained in accordance with the process described in Preparation B, replacing the benzaldehyde with 4-methoxybenzaldehyde in Step a. Melting point: 83° C.

Preparation F: 2-[2-(3-Fluorobenzyl)-5-methoxy-3-benzo[b]furyl]acetonitrile

The expected product is obtained in accordance with the process described in Preparation B, replacing the benzaldehyde with 3-fluorobenzaldehyde in Step a. Melting point: 67° C.

Preparation G: 2-[2-(3-Trifluoromethylbenzyl)-5-methoxy-3-benzo[b]furyl]-acetonitrile The expected product is obtained in accordance with the process described in Preparation B, replacing the benzaldehyde with 3-(trifluoromethyl)benzaldehyde in Step a. Melting point: 116° C.

Preparation H: 2-[2-(2,6-Dichlorobenzyl)-5-methoxy-3-benzo[b]furyl]acetonitrile

The expected product is obtained in accordance with the process described in Preparation B, replacing the benzaldehyde with 2,6-dichlorobenzaldehyde. Melting point: 184° C.

Preparation I: 2-(2-Furfuryl-5-methoxy-3-benzo[b]furyl)acetonitrile

The expected product is obtained in accordance with the process described in Preparation B, replacing the benzaldehyde with 2-furaldehyde.

Preparation J: 2-[5-Methoxy-2-(2-thienylmethyl)-3-benzo[b]furyl]acetonitrile

The expected product is obtained in accordance with the process described in Preparation B, replacing the benzaldehyde with 2-thiophenecarboxaldehyde.

Preparation K: 2-[5-Methoxy-2-(3-pyridylmethyl)-3-benzo[b]furyl]acetonitrile

The expected product is obtained in accordance with the process described in Preparation B, replacing the benzaldehyde with 3-pyridinecarboxaldehyde in Step a. Melting point: 123° C.

Preparation L: 2-[5-Methoxy-2-(3-phenylpropyl)-3-benzo[b]furyl]acetonitrile

The expected product is obtained in accordance with the process described in Preparation B, replacing the benzaldehyde with cinnamaldehyde in Step a.

Preparation M: 2-(5-Methoxy-2-propyl-3-benzo[b]furyl)acetonitrile

The expected product is obtained in accordance with the process described in Preparation B, replacing the benzaldehyde with acrolein in Step a.

Preparation N: 2-(2-Benzyl-5-ethyl-3-benzo[b]furyl)acetonitrile

The expected product is obtained in accordance with the process described in Preparation B, replacing the 5-methoxy-2,3-dihydro-3-benzo[b]furanone with 5-ethyl-2,3-dihydro-3-benzo[b]furanone in Step a.

Preparation O: 2-[5-Ethyl-2-(3-methoxybenzyl)-3-benzo[b]furyl]acetonitrile

The expected product is obtained in accordance with the process described in Preparation D, using as starting material 5-ethyl-2,3-dihydro-3-benzo[b]furanone.

Preparation P: 2-[5-Ethyl-2-(3-fluorobenzyl)-3-benzo[b]furyl]acetonitrile

The expected product is obtained in accordance with the process described in Preparation F, using as starting material 5-ethyl-2,3-dihydro-3-benzo[b]furanone.

Preparation Q: 2-(5-Ethyl-2-furfuryl-3-benzo[b]furyl)acetonitrile

The expected product is obtained in accordance with the process described in Preparation I, using as starting material 5-ethyl-2,3-dihydro-3-benzo[b]furanone.

Preparation R: 2-(2-Cyclohexylmethyl-5-methoxy-3-benzo[b]furyl)acetonitrile

The expected product is obtained in accordance with the process described in Preparation B, replacing the benzaldehyde with cyclohexanecarboxaldehyde in Step a. Melting point: 73° C.

Preparation S: 3-(5-Methoxy-2-furfuryl-3-benzo[b]furyl)butanenitrile

The expected product is obtained by the homologization of two carbon atoms of the chain carrying the nitrile function, using as starting material the compound described in Preparation I.

Preparation T: 4-(5-Methoxy-2-furfuryl-3-benzo[b]furyl)butanoic Acid

A solution of 3.5 mmol (1 g) of the compound described in Preparation S in 10 ml of methanol is heated at reflux in the presence of 10 ml of a 6M sodium hydroxide solution. After cooling, the reaction mixture is acidified with a 6M hydrochloric acid solution and the precipitate formed is filtered off. Recrystallisation from toluene yields the title compound.

Preparation U: 2-(5-Methoxy-2-phenyl-3-benzo[b]thienyl)acetonitrile

The expected product is obtained in accordance with the process described in Preparation A, replacing the 1-(4-methoxyphenoxy)-1-phenylacetone with 1-[(4-methoxyphenyl)-sulphanyl]-1-phenylacetone.

Preparation V: 2-(2-Benzyl-5-methoxy-3-benzo[b]thienyl)acetonitrile

The expected product is obtained in accordance with the process described in Preparation B, replacing the 5-methoxy-2,3-dihydro-3-benzo[b]furanone with 5-methoxy-2,3-dihydro-3-benzo[b]thiophenone.

Preparation W: 2-[5-Methoxy-2-(3-methoxybenzyl)-3-benzo[b]thienyl]acetonitrile The expected product is obtained in accordance with the process described in Preparation D, using as starting material 5-methoxy-2,3-dihydro-3-benzo[b]thiophenone.

Preparation X: 2-[2-(3-Fluorobenzyl)-5-methoxy-3-benzo[b]thienyl]acetonitrile The expected product is obtained in accordance with the process described in Preparation F, using as starting material 5-methoxy-2,3-dihydro-3-benzo[b]thiophenone.

Preparation Y: 2-[5-Methoxy-2-(2-thienylmethyl)-3-benzo[b]thienyl]acetonitrile The expected product is obtained in accordance with the process described in Preparation J, using a starting material 5-methoxy-2,3-dihydro-3-benzo[b]thiophenone.

Preparation Z: 2-[5-Methoxy-2-(3-pyridylmethyl)-3-benzo[b]thienyl]acetonitrile The expected product is obtained in accordance with the process described in Preparation K, using as starting material 5-methoxy-2,3-dihydro-3-benzo[b]thiophenone.

Preparation AA: 2-(5-Methoxy-2-propyl-3-benzo[b]thienyl)acetonitrile

The expected product is obtained in accordance with the process described in Preparation M, using as starting material 5-methoxy-2,3-dihydro-3-benzo[b]thiophenone.

Preparation AB: 2-(2-Cyclohexylmethyl-5-methoxy-3-benzo[b]thienyl)acetonitrile The expected product is obtained in accordance with the process described in Preparation R, using as starting material 5-methoxy-2,3-dihydro-3-benzo[b]thiophenone.

Preparation AC: 2-(2-Benzyl-5-ethyl-3-benzo[b]thienyl)acetonitrile

The expected product is obtained in accordance with the process described in Preparation N, using as starting material 5-ethyl-2,3-dihydro-3-benzo[b]thiophenone.

Preparation AD: 2-[2-(3-Chlorobenzyl)-5-methoxy-3-benzo[b]furyl]acetonitrile The expected product is obtained in accordance with the process described in Preparation B, replacing the benzaldehyde with 3-chlorobenzaldehyde in Step a. Melting point: 82° C.

Preparation AE: 2-[2-(3,5-Bistrifluoromethylbenzyl)-5-methoxy-3-benzo[b]furyl]-acetonitrile The expected product is obtained in accordance with the process described in Preparation B, replacing the benzaldehyde with 3,5-bistrifluoromethylbenzaldehyde in Step a. Melting point: 112° C.

EXAMPLE 1

N-[2-(5-Methoxy-2-phenyl-3-benzo[b]furyl)ethyl]acetamide

Step a: 3-(5-Methoxy-2-phenyl-3-benzo[b]furyl)ethylamine hydrochloride

Using an inert atmosphere, a solution of 6.84 mmol (1.8 g) of the compound described in Preparation A in 15 ml of tetrahydrofuran is added to 20.5 mmol (20 ml) of 1M borane-tetrahydrofuran complex. The reaction mixture is heated at reflux for 30 minutes, then 13 ml of 6M hydrochloric acid are added and the reaction mixture is heated at reflux for 30 minutes. After cooling and evaporating off the solvents, the residue obtained is washed with ether. The solid is filtered off to yield the expected compound. Melting point: 255° C. (decomposition)

Step b: N-[2-(5-Methoxy-2-phenyl-3-benzo[b]furyl)ethyl]acetamide 1.6 mmol (0.5 g) of the compound described in the preceding Step are dissolved in a mixture of 8 ml of dichloromethane and 4 ml of water. With vigorous stirring, 4.1 mmol (0.56 g) of potassium carbonate and 1.81 mmol (0.13 ml) of acetyl chloride are added in succession at 0° C. The reaction mixture is stirred at ambient temperature for 2 hours. The reaction mixture is extracted with dichloromethane, the combined organic phases are concentrated and the residue obtained is recrystallised from a toluene/cyclohexane mixture to yield the title product.

| | Melting point: 113–115° C. Elemental microanalysis | | |
|---|---|---|---|
| | C | H | N |
| % calc. | 73.77 | 6.19 | 4.53 |
| % found | 73.87 | 6.15 | 4.50 |

EXAMPLE 2

N-[2-(2-Benzyl-5-methoxy-3-benzo[b]furyl)ethyl]acetamide

The expected product is obtained in accordance with the process described in Example 1, using as starting material the compound described in Preparation B.

| | Melting point: 113–114° C. Elemental microanalysis: | | |
|---|---|---|---|
| | C | H | N |
| % calc. | 74.45 | 6.54 | 4.33 |
| % found | 74.08 | 6.68 | 4.09 |

EXAMPLE 3

N-{2-[5-Methoxy-2-(2-methoxybenzyl)-3-benzo[b]furyl]ethyl}acetamide

The expected product is obtained in accordance with the process described in Example 1, using as starting material the compound described in Preparation C.

| | Melting point: 103° C. Elemental microanalysis | | |
|---|---|---|---|
| | C | H | N |
| % calc. | 71.37 | 6.56 | 3.96 |
| % found | 71.28 | 6.53 | 4.03 |

EXAMPLE 4

N-{2-[5-Methoxy-2-(3-methoxybenzyl)-3-benzo[b]furyl]ethyl}acetamide

The expected product is obtained in accordance with the process described in Example 1, using as starting material the compound described in Preparation D.

| | Melting point: 110° C. Elemental microanalysis | | |
|---|---|---|---|
| | C | H | N |
| % calc. | 71.37 | 6.56 | 3.96 |
| % found | 71.32 | 6.49 | 4.02 |

EXAMPLE 5

N-{2-[5-Methoxy-2-(4-methoxybenzyl)-3-benzo[b]furyl]ethyl}acetamide

The expected product is obtained in accordance with the process described in Example 1, using as starting material the compound described in Preparation E.

| | Melting point: 102° C. Elemental microanalysis: | | |
|---|---|---|---|
| | C | H | N |
| % calc. | 71.37 | 6.56 | 3.96 |
| % found | 71.20 | 6.51 | 3.87 |

EXAMPLE 6

N-{2-[(3-Fluorobenzyl)-5-methoxy-3-benzo[b]furyl]ethyl}acetamide

The expected product is obtained in accordance with the process described in Example 1, using as starting material the compound described in Preparation F.

| | Melting point: 137° C. Elemental microanalysis: | | | |
|---|---|---|---|---|
| | C | H | N | F |
| % calc. | 70.37 | 5.90 | 4.10 | 5.57 |
| % found | 70.33 | 5.92 | 3.97 | 5.30 |

EXAMPLE 7

N-{2-[(3-Trifluoromethylbenzyl)-5-methoxy-3-benzo[b]furyl]ethyl}-acetamide

The expected product is obtained in accordance with the process described in Example 1, using as starting material the compound described in Preparation G.

| | Melting point: 124° C. Elemental microanalysis: | | | |
|---|---|---|---|---|
| | C | H | N | F |
| % calc. | 64.45 | 5.15 | 3.58 | 14.56 |
| % found | 64.60 | 5.19 | 3.53 | 14.55 |

EXAMPLE 8

N-{2-[(2,6-Dichlorobenzyl)-5-methoxy-3-benzo[b]furyl]ethyl}acetamide

The expected product is obtained in accordance with the process described in Example 1, using as starting material the compund described in Preparation H.

| | Melting point: 166° C. Elemental microanalysis: | | | |
|---|---|---|---|---|
| | C | H | N | Cl |
| % calc. | 61.24 | 4.88 | 3.57 | 18.07 |
| % found | 61.01 | 4.92 | 3.49 | 17.84 |

EXAMPLE 9

N-[2-(Furfuryl-5-methoxy-3-benzo[b]furyl)ethyl]acetamide

The expected product is obtained in accordance with the process described in Example 1, using as starting material the compound described in Preparation I.

EXAMPLE 10

N-{2-[5-Methoxy-2-(2-thienylmethyl)-3-benzo[b]furyl]ethyl}acetamide

The expected product is obtained in accordance with the process described in Example 1, using as starting material the compound described in Preparation J.

EXAMPLE 11

N-{2-[5-Methoxy-2-(3-pyridylmethyl)-3-benzo[b]furyl]ethyl}acetamide

The expected product is obtained in accordance with the process described in Example 1, using as starting material the compound described in Preparation K. Melting point: 117° C.

EXAMPLE 12

N-{2-[5-Methoxy-2-(3-phenylpropyl)-3-benzo[b]furyl]ethyl}acetamide

The expected product is obtained in accordance with the process described in Example 1, using as starting material the compound described in Preparation L.

Melting point: 102° C.
Elemental microanalysis:

|         | C     | H    | N    |
|---------|-------|------|------|
| % calc. | 75.19 | 7.17 | 3.99 |
| % found | 75.30 | 7.14 | 3.88 |

EXAMPLE 13

N[2-(5-Methoxy-2-propyl-3-benzo[b]furyl)ethyl]acetamide

The expected product is obtained in accordance with the process described in Example 1, using as starting material the compound described in Preparation M.

By proceeding as described in Example 1, using the compound described in Preparation B in Step a and the appropriate acid chloride in Step b the compounds of Examples 14 to 19 are obtained.

EXAMPLE 14

N-[2-(2-Benzyl-5-methoxy-3-benzo[b]furyl)ethyl]acrylamide

Melting point: 108–110° C.
Elemental microanalysis:

|         | C     | H    | N    |
|---------|-------|------|------|
| % calc. | 75.20 | 6.31 | 4.18 |
| % found | 74.95 | 6.37 | 4.22 |

EXAMPLE 15

N-[2-(2-Benzyl-5-methoxy-3-benzo[b]furyl)ethyl]-3-butenamide

Melting point: 97° C.
Elemental microanalysis:

|         | C     | H    | N    |
|---------|-------|------|------|
| % calc. | 75.62 | 6.63 | 4.01 |
| % found | 75.82 | 6.71 | 4.02 |

EXAMPLE 16

N-[2-(2-Benzyl-5-methoxy-3-benzo[b]furyl)ethyl]butanamide

Melting point: 86° C.
Elemental microanalysis:

|         | C     | H    | N    |
|---------|-------|------|------|
| % calc. | 75.19 | 7.17 | 3.99 |
| % found | 74.82 | 7.17 | 3.94 |

EXAMPLE 17

N-[2-(2-Benzyl-5-methoxy-3-benzo[b]furyl)ethyl]-2-phenylacetamide

EXAMPLE 18

N-[2-(2-Benzyl-5-methoxy-3-benzo[b]furyl)ethyl]trifluoroacetamide

EXAMPLE 19

N-[2-(2-Benzyl-5-methoxy-3-benzo[b]furyl)ethyl]iodoacetamide

Melting point: 135–136° C.
Elemental microanalysis:

|         | C     | H    | N    | I     |
|---------|-------|------|------|-------|
| % calc. | 53.46 | 4.48 | 3.11 | 27.26 |
| % found | 53.76 | 4.56 | 2.92 | 27.82 |

EXAMPLE 20

N-[2-(2-Benzyl-5-ethyl-3-benzo[b]furyl)ethyl]acetamide

The expected product is obtained in accordance with the process described in Example 1, using as starting material the compound described in Preparation N.

| | Melting point: 100–101° C. Elemental microanalysis: | | |
|---|---|---|---|
| | C | H | N |
| % calc. | 78.47 | 7.21 | 4.36 |
| % found | 78.29 | 7.12 | 4.18 |

EXAMPLE 21

N-{2-[5-Ethyl-2(3-methoxybenzyl)-3-benzo[b]furyl]ethyl}acetamide

The expected product is obtained in accordance with the process described in Example 1, using as starting material the compound described in Preparation O. Melting point: 102° C. Elemental microanalysis:

| | Melting point: 102° C. Elemental microanalysis: | | |
|---|---|---|---|
| | C | H | N |
| % calc. | 75.19 | 7.17 | 3.99 |
| % found | 75.04 | 7.17 | 3.96 |

EXAMPLE 22

N-{2-[5-Ethyl-2(3-fluorobenzyl)-3-benzo[b]furyl]ethyl}acetamide

The expected product is obtained in accordance with the process described in Example 1, using as starting material the compound described in Preparation P.

EXAMPLE 23

N-[2-(5-Ethyl-2furfuryl-3-benzo[b]furyl)ethyl]acetamide

The expected product is obtained in accordance with the process described in Example 1, using as starting material the compound described in Preparation Q.

EXAMPLE 24

N-[2-(2-Cyclohexylmethyl-5-methoxy-3-benzo[b]furyl)ethyl]acetamide

The expected product is obtained in accordance with the process described in Example 1, using as starting material the compound described in Preparation R.

| | Elemental microanalysis: | | |
|---|---|---|---|
| | C | H | N |
| % calc. | 72.92 | 8.26 | 4.25 |
| % found | 72.85 | 8.12 | 4.08 |

EXAMPLE 25

N-[2-(2-Benzyl-5-hydroxy-3-benzo[b]furyl)ethyl]acetamide

A solution of 12.4 mmol (3.9 g) of obron tribromide-dimethyl sulphide complex in 45 ml of dichloromethane is stirred for 15 minutes at ambient temperature. A solution of 6.2 mmol (2 g) of the compound described in Example 2 in 30 ml of dichloromethane is added to the above mixture and the reaction mixture is heated at reflux for one night. After cooling and hydrolysis, the dichloromethane is evaporated off. The mixture is extracted with ethyl acetate and the organic phase is washed with an aqueous 1M $NaHCO_3$ solution and then with an aqueous 1M sodium hydroxide solution. The aqueous phase so obtained is acidified and then extracted with ethyl acetate. The organic phase is dried and concentrated to yield the title compound.

EXAMPLE 26

N-[2-(2-Benzyl-5-pentyloxy-3-benzo[b]furyl)ethyl]acetamide

A solution of 1.9 mmol (0.6 g) of the compound described in Example 25 in 25 ml of acetone is heated at reflux for 15 minutes in the presence of 3.8 mmol (0.5 g) of potassium carbonate. 3.8 mmol (0.5 ml) of iodopentane are then added, and the reaction mixture is heated at reflux for one night. After cooling and filtration, the filtrate is concentrated. The residue obtained is taken up in a mixture of ethyl acetate and water and extracted. The organic phase is washed with a 20% sodium hydroxide solution and then with a saturated aqueous sodium chloride solution, and dried and concentrated to yield the expected compound.

| | Melting point: 71° C. Elemental microanalysis: | | |
|---|---|---|---|
| | C | H | N |
| % calc. | 75.96 | 7.70 | 3.69 |
| % found | 76.05 | 7.70 | 3.63 |

EXAMPLE 27

N-[2-(2-Benzyl-5-hexyloxy-3-benzo[b]furyl)ethyl]acetamide

The expected product is obtained in accordance with the process described in Example 26, replacing the iodopentane with bromohexane.

| | Melting point: 64° C. Elemental microanalysis: | | |
|---|---|---|---|
| | C | H | N |
| % calc. | 76.30 | 7.94 | 3.56 |
| % found | 76.15 | 7.93 | 3.58 |

EXAMPLE 28

N-[2-(2-Benzyl-5-cyclopropylmethoxy-3-benzo[b]furyl)ethyl]-acetamide

The expected product is obtained in accordance with the process described in Example 26, replacing the iodopentane with chloromethylcyclopropane.

EXAMPLE 29

N-{2-[2-Benzyl-5-(2-propynyloxy)-3-benzo[b]furyl]ethyl}acetamide

The expected product is obtained in accordance with the process described in Example 26, replacing the iodopentane with propargyl bromide.

EXAMPLE 30

N-{2-[2-Benzyl-1-(7H-furo[3,2-f]chromenyl)]ethyl}acetamide

A solution of 8.6 mmol (3 g) of the compound described in Example 29 in 100 ml of triethylene glycol is heated at 280° C. for 10 minutes. After cooling, the reaction mixture is poured into an ice/water mixture. After stirring, the precipitate formed is filtered off and the resulting solid is washed with water and recrystallised from a toluene/cyclohexane mixture to yield the expected compound.

EXAMPLE 31

N-{2-[2-Benzyl-1-(8,9-dihydro-7H-furo[3,2-f]chromenyl)]ethyl}-acetamide

A solution of 1.4 mmol (0.5 g) of the compound described in Example 30 in 25 ml of methanol is stirred for two hours under hydrogen atmospheric pressure in the presence of 0.05 g of Raney nickel. The catalyst is filtered off and the solvent is evaporated. The residue is recrystallised from a toluene/cyclohexane mixture to yield the title compound.

EXAMPLE 32

N-[2-(2-Benzyl-5-trifluoromethanesulphonyloxy-3-benzo[b]furyl)ethyl]-acetamide 6 ml of triethylamine are added to a solution of 6.5 mmol (2 g) of the compound described in Example 25 in 100 ml of dichloromethane. The reaction mixture is heated at reflux until dissolution occurs, then 9.1 mmol (3.25 g) of phenyl bis(trifluoromethanesulphonimide) and 7.2 mmol (1 g) of potassium carbonate are added. After 4 hours at reflux, the mixture is washed with 100 ml of 1M sodium hydrogen carbonate and then with 100 ml of 1M hydrochloric acid. The organic phase is dried, concentrated and purified by chromatography on silica gel, using ethyl acetate as eluant, to yield the expected compound.

EXAMPLE 33

N-[2-(2-Benzyl-5-phenyl-3-benzo[b]furyl)ethyl]acetamide 8.9 mmol (1.2 g) of phenylboric acid, 0.12 g of tetrakis(triphenylphosphine)palladium(0) and 0.6 g of lithium chloride are added to a solution of 5.9 mmol (2.5 g) of the compound described in Example 32 in 25 ml of dimethoxyethane under an inert atmosphere. The reaction mixture is stirred for 10 minutes and then 16 ml of a molar solution of sodium carbonate and 12 ml of absolute ethanol are added. The reaction mixture is heated at 90° C. for 4 hours. After cooling, 50 ml of 1M sodium carbonate are added and the reaction mixture is extracted twice with 50 ml of dichloromethane. The organic phase is dried, concentrated and purified by chromatography on silica gel, using ethyl acetate as eluant, to yield the expected compound.

The compounds of Examples 34 and 35 are obtained using the process described in Example 33 and the appropriate boric acid or tin compound.

EXAMPLE 34

N-[2-(2-Benzyl-5-furyl-3-benzo[b]furyl)ethyl]acetamide

EXAMPLE 35

N-[2-(2-Benzyl-5-vinyl-3-benzo[b]furyl)ethyl]acetamide

EXAMPLE 36

N-[2-(2-Benzyl-3-benzo[b]furyl)ethyl]acetamide

The expected product is obtained in accordance with the process described in Example 33, replacing the phenylboric acid with formic acid.

EXAMPLE 37

N-[3-(2-Furfuryl-5-methoxy-3-benzo[b]furyl)butyl]acetamide

The expected product is obtained in accordance with the process described in Example 1, using as starting material the compound described in Preparation S.

EXAMPLE 38

N-Methyl-4-(2-furfuryl-5-methoxy-3-benzo[b]furyl)butanamide

A solution of 1.5 mmol (0.5 g) of the compound described in Preparation T in 10 ml of dichloromethane is stirred at −10° C. for 20 minutes. 2.31 mmol (0.23 g) of triethylamine, 2.31 mmol (0.31 g) of HOBT and 2.31 mmol (0.44 g) of EDC are added in succession. The reaction mixture is stirred for 30 minutes at −10° C. and 3.1 mmol (0.20 g) of methylamine hydrochloride are added. The reaction mixture is stirred for 2 hours at ambient temperature. The mixture is concentrated and the residue is taken up in an ethyl acetate/water mixture. The organic phase is washed with a 0.1M hydrochloric acid solution, rinsed with water, washed with a 1M sodium hydroxide solution and then rinsed with water. After drying and concentration, the residue obtained is recrystallised from a toluene/petroleum ether mixture to yield the title product.

EXAMPLE 39

N-[2-(4-Formyl-5-methoxy-3-benzo[b]furyl)ethyl]acetamide

The expected product is obtained by formylation of N-[2-(5-methoxy-3-benzo[b]furyl)-ethyl]acetamide, using dichloromethyl methyl ether in the presence of aluminium trichloride.

Note: In the course of this process the compound formylated in the 6-position is also isolated.

EXAMPLE 40

N-[2-(5-Methoxy-4-trifluoromethanesulphonyloxy-3-benzo[b]furyl)-ethyl]acetamide

Step a: N-[2-(4-Hydroxy-5-methoxy-3-benzo[b]furyl)ethyl]acetamide

The expected product is obtained by Baeyer Villiger reaction starting from the compound described in Example 39.

Step b: N-[2-(5-Methoxy-4-trifluoromethanesulphonyloxy-3-benzo[b]furyl)ethyl]-acetamide The expected product is obtained in accordance with the process described in Example 32 starting from the compound described in the above Step.

The compounds of Examples 41 to 44 are obtained in accordance with the process described in Example 33, using as starting material the compound described in Example 40 and as reagent the appropriate boric acid or tin compound.

EXAMPLE 41

N-[2-(5-Methoxy-4-phenyl-3-benzo[b]furyl)ethyl]acetamide

EXAMPLE 42

N-{2-[5-Methoxy-4-(3-trifluoromethylphenyl)-3-benzo[b]furyl]ethyl}-acetamide

EXAMPLE 43

N-{2-[4-(2-Furyl)-5-methoxy-3-benzo[b]furyl]ethyl}acetamide

EXAMPLE 44

N-[2-(4-Benzyl-5-methoxy-3-benzo[b]furyl)ethyl]acetamide

EXAMPLE 45

N-[2-(6-Formyl-5-methoxy-3-benzo[b]furyl)ethyl]acetamide

The expected product is isolated in the course of the process described in Example 39.

EXAMPLE 46

N-[2-(5-Methoxy-6-trifluoromethanesulphonyloxy-3-benzo[b]furyl)-ethyl]acetamide

The expected product is obtained in accordance with the process described in Example 40, using as starting material the compound described in Example 45.

The compounds of Examples 47 to 50 are obtained in accordance with the process described in Example 33, using as starting material the compound described in Example 46 and as reagent the appropriate boric acid or tin compound.

EXAMPLE 47

N-[2-(5-Methoxy-6-phenyl-3-benzo[b]furyl)ethyl]acetamide

EXAMPLE 48

N-{2 -[5-Methoxy-6-(3-trifluoromethylphenyl)-3-benzo[b]furyl]ethyl}-acetamide

EXAMPLE 49

N-{2-[6-(2-Furyl)-5-methoxy-3-benzo[b]furyl]ethyl}acetamide

EXAMPLE 50

N-[2-(6-Benzyl-5-methoxy-3-benzo[b]furyl)ethyl]acetamide

EXAMPLE 51

N-[2-(5-Trifluoromethanesulphonyloxy-3-benzo[b]furyl)ethyl]-acetamide

Step a: N-[2-(5-Hydroxy-3-benzo[b]furyl)ethyl]acetamide

The expected product is obtained in accordance with the process described in Example 25, using as starting material N-[2-(5-methoxy-3-benzo[b]furyl)ethyl]acetamide.

Step b: N-[2-(5-Trifluoromethanesulphonyloxy-3-benzo[b]furyl)ethyl]acetamide

The expected product is obtained in accordance with the process described in Example 32, starting from the compound described in the above Step.

The compounds of Examples 52 to 56 are obtained in accordance with the process described in Example 33, using as starting material the compound described in Example 51 and the appropriate boric acid or tin compound.

EXAMPLE 52

N-[2-(5-Phenyl-3-benzo[b]furyl)ethyl]acetamide

EXAMPLE 53

N-[2-(5-Vinyl-3-benzo[b]furyl)ethyl]acetamide

EXAMPLE 54

N-{2-[5-(2-Furyl)-3-benzo[b]furyl]ethyl}acetamide

EXAMPLE 55

N-[2-(5-Benzyl-3-benzo[b]furyl)ethyl]acetamide

EXAMPLE 56

N-{2-[5-(2-Methoxyphenyl)-3-benzo[b]furyl]ethyl}acetamide

EXAMPLE 57

N-[2-(5-Methoxy-2-furfuryl-3-benzo[b]furyl)ethyl]-N'-methylurea

Step a: 2-(5-Methoxy-2-furfuryl-3-benzo[b]furyl)ethylamine

The expected product is obtained in accordance with the process described in Example 1, Step a, using as starting material the compound described in Preparation Q.

Step b: N-[2-(5-Methoxy-2-furfuryl-3-benzo[b]furyl)ethyl]-N'-methylurea

The expected product is obtained by the action of methyl isocyanate on the compound described in the above Step.

EXAMPLE 58

N-[2-(2-Benzyl-5-methoxy-3-benzo[b]furyl]ethyl}-N'-allylurea

The expected product is obtained in accordance with the process described in Example 57, using as starting material the compound described in Preparation B and replacing the methyl isocyanate with allyl isocyanate.

The compounds of Examples 59 to 63 are obtained using Lawesson's reagent, starting from the products described in the above Examples.

EXAMPLE 59

N-[2-(2-Benzyl-5-methoxy-3-benzo[b]furyl)ethyl]thioacetamide

EXAMPLE 60

N-[2-(5-Methoxy-2-phenyl-3benzo[b]furyl)ethyl]thioacetamide

EXAMPLE 61

N-{2-[5-Methoxy-2-(3-methoxybenzyl)-3-benzo[b]furyl]ethyl}-thioacetamide

EXAMPLE 62

N-{2-[5-Methoxy-2-(3-pyridylmethyl)-3-benzo[b]furyl]ethyl}-thioacetamide

EXAMPLE 63

N-[2-(2-Benzyl-5-ethyl-3-benzo[b]furyl)ethyl]thioacetamide

EXAMPLE 64

N-[2-(5-Methoxy-2-phenyl-3-benzo[b]thienyl)ethyl]acetamide

The expected product is obtained in accordance with the process described in Example 1, using as starting material the compound described in Preparation U.

EXAMPLE 65

N-[2-(2-Benzyl-5-methoxy-3-benzo[b]thienyl)ethyl]acetamide

The expected product is obtained in accordance with the process described in Example 1, using as starting material the compound described in Preparation V.

EXAMPLE 66

N-{2-[5-Methoxy-2-(3-methoxybenzyl)-3-benzo[b]thienyl]ethyl}-acetamide

The expected product is obtained in accordance with the process described in Example 1, using as starting material the compound described in Preparation W.

EXAMPLE 67

N-{2-[2-(3-Fluorobenzyl)-5-methoxy-3-benzo[b]thienyl]ethyl}acetamide

The expected product is obtained in accordance with the process described in Example 1, using as starting material the compound described in Preparation X.

EXAMPLE 68

N-{2-[5-Methoxy-2-(2-thienylmethyl)-3-benzo[b]thienyl]ethyl}-acetamide

The expected product is obtained in accordance with the process described in Example b 1, using as starting material the compound described in Preparation Y.

EXAMPLE 69

N-{2-[5-Methoxy-2-(3-pyridylmethyl)-3-benzo[b]thienyl]ethyl}-acetamide

The expected product is obtained in accordance with the process described in Example 1, using as starting material the compound described in Preparation Z.

EXAMPLE 70

N-[2-(5-Methoxy-2-propyl-3-benzo[b]thienyl)ethyl]acetamide

The expected product is obtained in accordance with the process described in Example 1, using as starting material the compound described in Preparation AA.

EXAMPLE 71

N-[2-(2-Cyclohexylmethyl-5-methoxy-3-benzo[b]thienyl)ethyl]acetamide

The expected product is obtained in accordance with the process described in Example 1, using as starting material the compound described in Preparation AB.

Using the product described in Example 1, starting from the compound described in Preparation V and selecting as reagent the appropriate acid chloride, the compounds of Examples 72 to 75 are obtained.

EXAMPLE 72

N-[2-(2-Benzyl-5-methoxy-3benzo[b]thienyl)ethyl]acrylamide

EXAMPLE 73

N-[2-(2-Benzyl-5methoxy-3benzo[b]thienyl)ethyl]butanamide

EXAMPLE 74

N-[2-(2-Benzyl-5-methoxy-3benzo[b]thienyl)ethyl]-2-phenylacetamide

EXAMPLE 75

N-[2-(2-Benzyl-5-methoxy-3-benzo[b]thienyl)ethyl]iodacetamide

EXAMPLE 76

N-[2-(2-Benzyl-5-ethyl-3benzo[b]thienyl)ethyl]acetamide

The expected product is obtained in accordance with the process described in Example 1, using as starting material the compound described in Preparation AC.

EXAMPLE 77

N-[2-(2-Benzyl-5-hydroxy-3-benzo[b]thienyl)ethyl]acetamide

The expected product is obtained in accordance with the process described in Example 25, using as starting material the compound described in Example 65.

EXAMPLE 78

N-[2-(2-Benzyl-5-hexyloxy-3-benzo[b]thienyl)ethyl]acetamide

The expected product is obtained in accordance with the process described in Example 27, using as starting material the compound described in Example 77.

EXAMPLE 79

N-{2-[2-Benzyl-5-2-propynyloxy)-3-benzo[b]thienyl]ethyl}acetamide

The expected product is obtained in accordance with the process described in Example 29, using as starting material the compound described in Example 77.

EXAMPLE 80

N-{2-[2-Benzyl-1-(7H-thieno[3,2-f]chromenyl)]ethyl}acetamide

The expected product is obtained in accordance with the process described in Example 30, using as starting material the compound described in Example 79.

EXAMPLE 81

N-{2-[2-Benzyl-1-(8,9-dihydro-7H-thieno[3,2-f]chromenyl)]ethyl}-acetamide

The expected product is obtained in accordance with the process described in Example 31, using as starting material the compound described in Example 80.

EXAMPLE 82

N-[2-(2-Benzyl-5-trifluoromethanesulphonyloxy-3-benzo[b]thienyl)-ethyl]acetamide The expected product is obtained in accordance with the process described in Example 32, using as starting material the compound described in Example 77.

The compounds of Examples 83 to 85 are obtained in accordance with the process described in Example 33, using as starting material the compound described in Example 82 and as reagent the appropriate boric acid or tin compound.

EXAMPLE 83

N-[2-(2-Benzyl-5-phenyl-3-benzo[b]thienyl)ethyl]acetamide

EXAMPLE 84

N-{2-[2-Benzyl-5-(2-furyl)-3-benzo[b]thienyl]ethyl}acetamide

EXAMPLE 85

N-[2-(2-Benzyl-5-vinyl-3-benzo[b]thienyl)ethyl]acetamide

EXAMPLE 86

N-[2-(2-Benzyl-3-benzo[b]thienyl)ethyl]acetamide

The expected product is obtained in accordance with the process described in Example 36, using as starting material the compound described in Example 82.

EXAMPLE 87

N-[2-(4-Formyl-5-methoxy-3-benzo[b]thienyl)ethyl]acetamide

The expected product is obtained in accordance with the process described in Example 39, using as starting material N-[2-(5-methoxy-3-benzo[b]thienyl)ethyl]acetamide Note: In the course of this process the compound formylated in the 6-position is also isolated.

EXAMPLE 88

N-[2-(5-Methoxy-4-trifluoromethanesulphonyloxy-3-benzo[b]thienyl)-ethyl]acetamide The expected product is obtained in accordance with the process described in Example 40, using as starting material the compound described in Example 87.

The compounds of Examples 89 to 91 are obtained in accordance with the process described in Example 33, using as starting material the compound described in Example 88 and as reagent the appropriate boric acid or tin compound.

EXAMPLE 89

N-[2-(5-Methoxy-4-phenyl-3-benzo[b]thienyl)ethyl]acetamide

EXAMPLE 90

N-{2-[4-(2-Furyl)-5-methoxy-3-benzo[b]thienyl]ethyl}acetamide

EXAMPLE 91

N-[2-(4-Benzyl-5-methoxy-3-benzo[b]thienyl)ethyl]acetamide

EXAMPLE 92

N-[2-(6-Formyl-5-methoxy-3-benzo[b]thienyl)ethyl]acetamide

The expected product is isolated in the process described in Example 87.

EXAMPLE 93

N-[2-(5-Methoxy-6-trifluoromethanesulphonyloxy-3-benzo[b]thienyl)-ethyl]acetamide The expected product is obtained in accordance with the process described in Example 40, using as starting material the compound described in Example 92.

The compound of Examples 94 to 96 are obtained in accordance with the process described in Example 33, using as starting material the compound described in Example 93 and as reagent the appropriate boric acid or tin compound.

EXAMPLE 94

N-[2-(5-Methoxy-6-phenyl-3-benzo[b]thienyl)ethyl]acetamide

EXAMPLE 95

N-{2-[6-(2-Furyl)-5-methoxy-3-benzo[b]thienyl]ethyl}acetamide

EXAMPLE 96

N-[2-(6-Benzyl-5-methoxy-3-benzo[b]thienyl)ethyl]acetamide

EXAMPLE 97

N-[2-(5-Trifluoromethanesulphonyloxy-3-benzo[b]thienyl)ethyl]-acetamide

The expected product is obtained in accordance with the process described in Example 51, using as starting material N-[2-(5-methoxy-3-benzo[b]thienyl)ethyl]acetamide The compounds of Examples 98 to 102 are obtained in accordance with the process described in Example 33, using as starting material the compound described in Example 97 and as reagent the appropriate boric acid or tin compound.

EXAMPLE 98

N-[2-(5-Phenyl-3-benzo[b]thienyl)ethyl]acetamide

EXAMPLE 99

N-[2-(5-Vinyl-3-benzo[b]thienyl)ethyl]acetamide

EXAMPLE 100

N-[2-(5-Benzyl-3-benzo[b]thienyl)ethyl]acetamide

EXAMPLE 101

N-{2-[5-(2-Furyl)-3-benzo[b]thienyl]ethyl}acetamide

EXAMPLE 102

N-[2-(2-Benzyl-5-methoxy-3-benzo[b]thienyl)ethyl]-N'-allylurea

The expected product is obtained in accordance with the process described in Example 57, using as starting material the compound described in Preparation V, and replacing the methyl isocyanate with allyl isocyanate.

The compounds of Examples 104 to 105 are obtained using Lawesson's reagent, starting from the products described in the above Examples.

EXAMPLE 103

N-[2-(5-Methoxy-2-phenyl-3-benzo[b]thienyl)ethyl]thioacetamide

EXAMPLE 104

N-{2-[5-Methoxy-2-(3-methoxybenzyl)-3-benzo[b]thienyl]ethyl}thioacetamide

EXAMPLE 105

N-[2-(2-Benzyl-5-ethyl-3-benzo[b]thienyl)ethyl]thioacetamide

Using the product described in Example 1, and replacing the acetyl chloride in Step b with the appropriate acid chloride, the compounds of Examples 106 to 108 are obtained.

EXAMPLE 106

N-[2-(5-Methoxy-2-phenyl-3-benzo[b]furyl)ethyl]acrylamide

Melting point: 117° C.
Elemental microanalysis:

|         | C     | H    | N    |
|---------|-------|------|------|
| % calc. | 74.75 | 5.96 | 4.36 |
| % found | 74.47 | 5.94 | 4.27 |

EXAMPLE 107

N-[2-(5-Methoxy-2-phenyl-3-benzo[b]furyl)ethyl]-3-butenamide

Melting point: 100° C.
Elemental microanalysis:

|         | C     | H    | N    |
|---------|-------|------|------|
| % calc. | 75.20 | 6.31 | 4.18 |
| % found | 75.05 | 6.38 | 4.05 |

EXAMPLE 108

N-[2-(5-Methoxy-2-phenyl-3-benzo[b]furyl)ethyl]-2-butenamide

Melting point: 119° C.
Elemental microanalysis:

|         | C     | H    | N    |
|---------|-------|------|------|
| % calc. | 75.20 | 6.31 | 4.18 |
| % found | 75.13 | 6.34 | 4.25 |

EXAMPLE 109

N-{2-[5-Methoxy-2-(3-methoxybenzyl)-3-benzo[b]furyl]ethyl}acrylamide

The expected product is obtained in accordance with the process described in Example 1, using as starting material the compound described in Preparation D and replacing the acyl chloride in Step b with acryloyl chloride.

Melting point: 114° C.
Elemental microanalysis:

|         | C     | H    | N    |
|---------|-------|------|------|
| % calc. | 72.31 | 6.35 | 3.83 |
| % found | 72.69 | 6.40 | 3.81 |

EXAMPLE 110

N-{2-[2-(3-Chlorobenzyl)-5-methoxy-3-benzo[b]furyl]ethyl}acetamide

The expected product is obtained in accordance with the process described in Example 1, using as starting material the compound described in Preparation AD.

Melting point: 115° C.
Elemental microanalysis:

|         | C     | H    | N    | Cl   |
|---------|-------|------|------|------|
| % calc. | 67.13 | 5.63 | 3.91 | 9.91 |
| % found | 67.02 | 5.70 | 3.85 | 9.75 |

EXAMPLE 111

N-{2-[2-(3,5-Bistrifluoromethylbenzyl)-5-methoxy-3-benzo[b]furyl]-ethyl}acetamide The expected product is obtained in accordance with the process described in Example 1, using as starting material the compound described in Preparation AE.

| | Melting point: 125° C. | | | |
|---|---|---|---|---|
| | Elemental microanalysis | | | |
| | C | H | N | F |
| % calc. | 57.52 | 4.17 | 3.05 | 24.81 |
| % found | 57.27 | 4.09 | 3.08 | 24.75 |

PHARMACOLOGICAL STUDY

EXAMPLE A

Acute Toxicity Study

Acute toxicity was evaluated after oral administration to groups each comprising 8 mice (26±2 grams). The animals were observed at regular intervals during the course of the first day, and daily for the two weeks following treatment. The $LD_{50}$ (dose that causes the death of 50% of the animals) was evaluated and demonstrated the low toxicity of the compounds of the invention.

EXAMPLE B

Melatonin Receptor Binding Study on Pars Tuberalis Cells of Sheep

Melatonin receptor binding studies of the compounds of the invention were carried out according to conventional techniques on pars tuberalis cells of sheep. The pars tuberalis of the adenohypophysis is in fact characterised in mammals by a high density of melatonin receptors (Journal of Neuroendocrinology, 1, pp. 1–4, 1989).

Protocol

1) Sheep pars tuberalis membranes are prepared and used as target tissue in saturation experiments to determine the binding capacities and affinities for 2-$[^{125}I]$-iodomelatonin.

2) Sheep pars tuberalis membranes are used as target tissue in competitive binding experiments using the various test compounds in comparison with melatonin.

Each experiment is carried out in triplicate and a range of different concentrations is tested for each compound. The results, after statistical processing, enable the binding affinities of the compound tested to be determined.

Results

The compounds of the invention appear to have a strong affinity for melatonin receptors.

EXAMPLE C

Melatonin $MEL_{1a}$ and $MEL_{1b}$ Receptor Binding Study

The $MEL_{1a}$ or $MEL_{1b}$ receptor binding experiments are carried out using 2-$[^{125}I]$-melatonin as reference radioligand. The radioactivity retained is determined using a Beckman® LS6000 liquid scintillation counter.

Competitive binding experiments are then carried out in triplicate using the various test compounds. A range of different concentrations is tested for each compound. The results enable the binding affinities of the compounds tested ($IC_{50}$) to be determined.

The $IC_{50}$ values found for the compounds of the invention show that the binding of the compounds tested is very strong for one or other of the $MEL_{1a}$ and $MEL_{1b}$ receptor subtypes, the values being in a range from 0.1 to 10 nM.

EXAMPLE D

Four Plate Test

The products of the invention are administered by the oesophageal route to groups each comprising ten mice. One group is given syrup of gum. Thirty minutes after administration of the products to be studied, the animals are placed in cages in which the floor is composed of four metal plates. Each time the animal passes from one plate to another it receives a light electric shock (0.35 mA). The number of passages from one plate to another in one minute is recorded. After administration, the compounds of the invention significantly increase the number of passages from one plate to another, demonstrating the anxiolytic activity of the compounds of the invention.

EXAMPLE E

Action of the Compounds of the Invention on the Circadian Rhythms of Locomotive Activity of the Rat The involvement of melatonin in influencing, by day/night alternation, the majority of physiological, biochemical and behavioural circadian rhythms has made it possible to establish a pharmacological model for research into melatoninergic ligands.

The effects of the molecules are tested in relation to numerous parameters and, in particular, in relation to the circadian rhythms of locomotive activity, which represent a reliable marker of the activity of the endogenous circadian clock.

In this study, the effects of such molecules on a particular experimental model, namely the rat placed in temporal isolation (permanent darkness), are evaluated.

Experimental protocol

One-month-old Long Evans male rats are subjected, as soon as they arrive at the laboratory, to a light cycle of 12 hours of light per 24 hours (LD 12:12).

After 2 to 3 weeks' adaptation, they are placed in cages fitted with a wheel connected to a recording system in order to detect the phases of locomotive activity and thus monitor the nychthemeral (LD) or circadian (DD) rhythms.

As soon as the rhythms recorded show a stable pattern in the light cycle LD 12:12, the rats are placed in permanent darkness (DD).

Two or three weeks later, when the free course (rhythm reflecting that of the endogenous clock) is clearly established, the rats are given a daily administration of the molecule to be tested.

The observations are made by means of visualisation of the rhythms of activity:

influence on the rhythms of activity by the light rhythm, disappearance of the influence on the rhythms in permanent darkness, influence by the daily administration of the molecule; transitory or durable effect.

A software package makes it possible:

to measure the duration and intensity of the activity, the period of the rhythm of the animals during free course and during treatment, possibly to demonstrate by spectral analysis the existence of circadian and non-circadian (for example ultradian) components.

Results:

The compounds of the invention clearly appear to allow powerful action on the circadian rhythm via the melatoninergic system.

EXAMPLE F

Anti-arrhythmic Activity

Protocol (Ref: LAWSON J. W. et al. J. Pharmacol. Expert. Therap., 1968, 160, pp. 22–31)

The test substance is administered intraperitoneally to a group of 3 mice 30 minutes before being subjected to anaesthesia with chloroform. The animals are then observed for 15 minutes. The absence of recording of arrhythmia and of cardiac frequencies higher than 200 beats/min (control: 400–480 beats/min) in at least two animals indicates significant protection.

EXAMPLE G

Pharmaceutical Composition: Tables

| | |
|---|---|
| 1000 tablets each comprising 5 mg of the compound of Example 4 | 5 g |
| wheat starch | 20 g |
| maize starch | 20 g |
| lactose | 30 g |
| magnesium stearate | 2 g |
| silica | 1 g |
| hydroxypropyl cellulose | 2 g |

We claim:

1. A compound selected from those of formula (I):

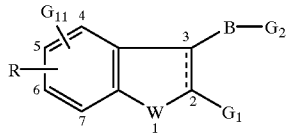

(I)

wherein:

the 2–3 bond is saturated or unsaturated

W represents oxygen or sulphur,

B represents linear or branched $(C_1–C_6)$-alkylene optionally substituted by one or more linear or branched $(C_1–C_6)$-alkyl, hydroxy, linear or branched $(C_1–C_6)$-alkoxy, carboxy, or linear or branched $(C_1–C_6)$-alkoxycarbonyl, R represents hydrogen, hydroxy, R' or OR', R', representing optionally substituted linear or branched $(C_1–C_6)$-alkyl, optionally substituted linear or branched $(C_2–C_6)$-alkenyl, optionally substituted linear or branched $(C_2–C_6)$-alkynyl, optionally substituted $(C_3–C_7)$-cycloalkyl, linear or branched $(C_1–C_6)$-trihaloalkylsulphonyl, optionally substituted aryl, optionally substituted biphenyl, or optionally substituted heteroaryl, $G_1$ represents halogen, linear or branched $(C_1–C_6)$-trihaloalkylsulphonyloxy, carboxy, formyl, cyano, $R_1$, —CO—$R_1$ or —O—CO—$R_1$, $R_1$ representing an optionally substituted linear or branched $(C_1–C_6)$-alkyl, optionally substituted linear or branched $(C_2–C_6)$-alkenyl, optionally substituted linear or branched $(C_2–C_6)$-alkynyl, optionally substituted $(C_3–C_7)$-cycloalkyl, optionally substituted aryl, optionally substituted biphenyl, or optionally substituted heteroaryl, in which case $G_{11}$ represents hydrogen or $G_{11}$ and R form together with the carbon atoms carrying them a ring having to 7 members that is saturated or unsaturated and contains oxygen, that ring optionally being substituted by one or more groups selected from linear or branched $(C_1–C_6)$-alkyl, linear or branched $(C_1–C_6)$-alkoxy, hydroxy, oxo, carboxy, and linear or branched $(C_1–C_6)$-alkoxycarbonyl, or $G_1$ represents hydrogen, in which case $G_{11}$ represents linear or branched $(C_1–C_6)$-trihaloalkylsulphonyloxy, carboxy, formyl, cyano, $R_1$, —CO—$R_1$, or —O—CO—$R_1$, $R_1$ representing optionally substituted linear or branched $(C_1–C_6)$-alkyl, optionally substituted linear or branched $(C_2–C_6)$-alkenyl, optionally substituted linear or branched $(C_2–C_6)$-alkynyl, optionally substituted $(C_3–C_7)$-cycloalkyl, optionally substituted aryl, optionally substituted biphenyl or optionally substituted heteroaryl, $G_2$ represents a group selected from:

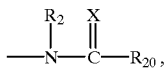

($G_{20}$)

($G_{21}$)

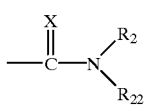

($G_{22}$)

wherein:

X represents oxygen or sulphur, $R_2$ represents hydrogen or linear or branched $(C_1–C_6)$-alkyl, $R_{20}$, $R_{21}$ and $R_{22}$ each represents optionally substituted linear or branched $(C_1–C_6)$-alkyl, optionally substituted linear or branched $(C_2–C_6)$-alkenyl, optionally substituted linear or branched $(C_2–C_6)$-alkynyl, optionally substituted $(C_3–C_7)$-cycloalkyl, optionally substituted heteroaryl, optionally substituted aryl, or optionally substituted biphenyl.

provided that:

when $G_2$ represents $G_{22}$ wherein $R_{22}$ as defined above is other than optionally substituted aryl, optionally substituted heteroaryl, or optionally substituted biphenyl, then $G_1$ or $G_{11}$ represents heteroaryl other than pyridyl that is optionally substituted, linear or branched $(C_1–C_6)$-alkyl substituted by heteroaryl other than pyridyl that is optionally substituted, —CO—$R_1$ or O—CO—$R_1$, $R_1$ being as defined above, when $G_2$ represents $G_{20}$ or $G_{21}$ wherein $R_{20}$ and $R_{21}$ are other than optionally substituted aryl, optionally substituted biphenyl, or optionally substituted heteroaryl, and $G_1$ is other than optionally substituted heteroaryl or optionally substituted naphthyl, or $G_{11}$ is other than optionally substituted heteroaryl or optionally substituted naphthyl while R represents hydrogen, then B represents optionally substituted methylene or ethylene, when $G_2$ represents $G_{20}$ or $G_{21}$, $R_{20}$ or $R_{21}$ as defined above being other than optionally substituted aryl or optionally substituted heteroaryl and:
- →when R and $G_1$ each represents hydrogen, then $G_{11}$ is other than linear or branched ($C_1$–$C_6$)-alkyl, other than ($C_3$–$C_7$)-cycloalkyl optionally substituted by one or more halogen, hydroxy, and other than linear or branched ($C_1$–$C_6$)-alkyl substituted by one or more halogen, hydroxy, linear or branched ($C_1$–$C_6$)-alkoxy, or ($C_3$–$C_7$)-cycloalkyl optionally substituted by one or more halogen or hydroxy,
- →when $G_1$ represents hydrogen and R represents OR', R' as defined above being other than optionally substituted heteroaryl, then $G_{11}$ is other than linear or branched ($C_1$–$C_6$)-alkyl, linear or branched ($C_2$–$C_6$)-alkenyl, or linear or branched ($C_2$–$C_6$)-alkynyl, when $G_2$ represents either $G_{21}$, wherein $R_{21}$ is other than optionally substituted linear or branched ($C_2$–$C_6$)-alkenyl and other than optionally substituted ($C_2$–$C_6$)-alkynyl, or $G_{20}$, wherein $R_{20}$ represents ($C_3$–$C_7$)-cycloalkyl optionally substituted by one or more halogen, hydroxy or linear or branched ($C_1$–$C_6$)-alkoxy, or linear or branched ($C_1$–$C_6$)-alkyl substituted by ($C_3$–$C_7$)-cycloalkyl optionally substituted by one or more halogen, hydroxy or linear or branched ($C_1$–$C_6$)-alkoxy, then:
- →$G_{11}$ is other than linear or branched ($C_1$–$C_6$)-alkyl,
- →$G_1$ is other than halogen, linear or branched ($C_1$–$C_6$)-alkyl, linear or branched ($C_1$–$C_6$)-alkyl substituted by optionally substituted phenyl, and other than optionally substituted phenyl, when $G_2$ represents $G_{21}$, X representing sulphur and B representing ethylene, then $R_{21}$ is other than optionally substituted aryl, the term "aryl" denoting phenyl or naphthyl, the term "heteroaryl" denoting a saturated or unsaturated, 4- to 11-membered, mono- or bi-cyclic group containing from 1 to 4 hetero atoms selected nitrogen, oxygen, and sulphur, is being understood that:

the expression "optionally substituted" applied to the terms "alkyl", "alkenyl", "alkynyl", and "cycloalkyl" means that those groups are, if desired, substituted by one or more halogen or ($C_3$–$C_7$)-cycloalkyl, hydroxy, linear or branched ($C_1$–$C_6$)-alkoxy, optionally substituted aryl and/or optionally substituted heteroaryl, the expression "optionally substituted" applied to the terms "aryl", "biphenyl", and "heteroaryl" means that those groups are, if desired, substituted by one or more halogen and/or linear or branched ($C_1$–$C_6$)-alkyl, linear or branched ($C_1$–$C_6$)-trihaloalkyl, hydroxy, linear or branched ($C_1$–$C_6$)-alkoxy, nitro, amino which is optionally substituted by one or two identical or different, linear or branched ($C_1$–$C_6$)-alkyl; linear or branched ($C_1$–$C_6$)-alkylcarbonyl, cyano, carboxy, and/or aminocarbonyl optionally substituted by one or two identical or different linear or branched ($C_1$–$C_6$)-alkyl, their enantiomers and diastereoisomers, and also pharmaceutically acceptable addition salts thereof with an acid or base.

2. A compound of claim 1, wherein the 2–3 bond is unsaturated.

3. A compound of claim 1, wherein W represents oxygen.

4. A compound of claim 1, wherein W represents sulphur.

5. A compound of claim 1, wherein B represents linear or branched ($C_1$–$C_6$)-alkylene.

6. A compound of claim 1, wherein $G_{11}$ represents hydrogen.

7. A compound of claim 1, wherein $G_1$ and R each represents hydrogen.

8. A compound of claim 1, wherein R is attached in the 5-position of the heterocyclic ring structure.

9. A compound of claim 1, wherein $G_{11}$ is attached in the 5-position of the heterocyclic ring structure.

10. A compound of claim 1, wherein R represents hydrogen, R' or OR' wherein R' represents linear or branched ($C_1$–$C_6$)-alkyl, linear or branched ($C_2$–$C_6$)-alkenyl or linear or branched ($C_2$–$C_6$)-alkynyl.

11. A compound of claim 1, wherein $G_1$ represents optionally substituted aryl, optionally substituted heteroaryl, or linear or branched ($C_1$–$C_6$)-alkyl substituted by a group selected from ($C_3$–$C_7$)-cycloalkyl, optionally substituted aryl and optionally substituted heteroaryl.

12. A compound of claim 1, wherein $G_1$ represents methylene substituted by optionally substituted phenyl.

13. A compound of claim 1, wherein $G_{11}$ represents optionally substituted aryl, optionally substituted heteroaryl, or linear or branched ($C_1$–$C_6$)-alkyl substituted by a group selected from ($C_3$–$C_7$)-cycloalkyl, optionally substituted aryl and optionally substituted heteroaryl.

14. A compound of claim 1, wherein $G_2$ is such that X represent oxygen, $R_2$ represents hydrogen, and $R_{20}$, $R_{21}$ and $R_{22}$ are selected from linear or branched ($C_2$–$C_6$)-alkenyl, and linear or branched ($C_1$–$C_6$)-alkyl optionally substituted by one or more halogen.

15. A compound of claim 1, wherein the 2–3 bond is unsaturated, W represents oxygen, B represents ethylene, R attached in the 5-position of the heterocyclic ring structure, represents hydrogen, R' or OR' wherein R' is linear or branched ($C_1$–$C_6$)-alkyl $G_{11}$ represents hydrogen, $G_1$ represents optionally substituted aryl, optionally substituted heteroaryl, or linear or branched ($C_1$–$C_6$)-alkyl substituted by ($C_3$–$C_7$)-cycloalkyl, by optionally substituted aryl, or by optionally substituted heteroaryl, and $G_2$ represents $G_{20}$ wherein X represents oxygen, $R_2$ represents hydrogen and $R_{20}$ represents linear or branched ($C_2$–$C_6$)-alkenyl, or linear or branched ($C_1$–$C_6$)-alkyl optionally substituted by one or more halogen.

16. A compound of claim 1, wherein the 2–3 bond is unsaturated, W represents oxygen, B represents ethylene, R and $G_1$ each represents hydrogen, $G_{11}$, attached in the 5-position of the heterocyclic ring structure, represents optionally substituted aryl, optionally substituted heteroaryl, or linear or branched ($C_1$–$C_6$)-alkyl substituted by optionally substituted aryl or by optionally substituted heteroaryl, and $G_2$ represents $G_{20}$ wherein X represents oxygen, $R_2$ represents hydrogen and $R_{20}$ represents linear or branched ($C_2$–$C_6$)-alkenyl, or linear or branched ($C_1$–$C_6$)-alkyl optionally substituted by one or more halogen.

17. A compound of claim 1, wherein the 2–3 bond is unsaturated, W represents sulfur, B represents ethylene, R, attached in the 5-position of the heterocyclic ring structure, represents hydrogen, R' or OR' wherein R' is linear or branched ($C_1$–$C_6$)-alkyl $G_{11}$ represents hydrogen, $G_1$ represents optionally substituted aryl, optionally substituted heteroaryl, or linear or branched ($C_1$–$C_6$)-alkyl substituted by ($C_3$–$C_7$)-cycloalkyl, by optionally substituted aryl or by optionally substituted heteroaryl, and $G_2$ represents $G_{20}$ wherein X represents oxygen, $R_2$ represents hydrogen and $R_{20}$ represents linear or branched ($C_2$–$C_6$)-alkenyl, or linear or branched ($C_1$–$C_6$)-alkyl optionally substituted by one or more halogen.

18. A compound of claim 1, wherein the 2–3 bond is unsaturated, W represents sulfur, B represents ethylene, R and $G_1$ each represent hydrogen, $G_{11}$, attached in the 5-position of the heterocyclic ring structure, represents optionally substituted aryl, optionally substituted heteroaryl, or linear or branched ($C_1$–$C_6$)-alkyl substituted by optionally substituted aryl or by optionally substituted heteroaryl, and $G_2$ represents $G_{20}$ wherein X represents oxygen, $R_2$ represents hydrogen and $R_{20}$ represents linear or branched ($C_2$–$C_6$)-alkenyl, or linear or branched ($C_1$–$C_6$)-alkyl optionally substituted by one or more halogen.

19. A compound of claim 1, which is N-[2-(2-benzyl-5-methoxy-3-benzo[b]furyl)ethyl]acrylamide.

20. A compound of claim 1, selected from the group consisting of:

N-{2-[5-methoxy-2-(3-methoxybenzyl)-3-benzo[b]furyl]ethyl}acetamide and

N-{2-[5-methoxy-2-(3-trifluoromethylbenzyl)-3-benzo[b]furyl]ethyl}acetamide.

21. A compound of claim 1, which is N-{(2-[5-methoxyphenyl)-3-benzo[b]furyl]ethyl}acetamide.

22. A pharmaceutical composition useful in the treatment of disease associated with the melatoninergic system comprising as active principle an effective amount of a compound as claimed in claim 1, together with one or more pharmaceutically acceptable excipients or vehicles.

23. A method for treating a living body afflicted with a disease associated with the melatoninergic system comprising the step of administering to the living body an amount of a compound of claim 1 which is effective for alleviation of said disease.

* * * * *

UNITED STATES PATENT AND TRADEMARK OFFICE
CERTIFICATE OF CORRECTION

PATENT NO.  : 6,147,110
DATED       : November 14, 2000                      Page 1 of 5
INVENTOR(S) : D. Lesieur, N. Ruiz, V. Wallez, S. Boye,
              C. Bennejean, P. Renard, P. Delagrange It is certified that error appears in the above-identified patent and that said Letters Patent is hereby corrected as shown below:

Title Page, [57] ABSTRACT, 3rd line from bottom:
   "wherein $R_{20}$, $R_{21}$, and $R_2$" should read:
   -- wherein $R_{20}$, $R_{21}$, $R_{22}$ and $R_2$ --.
   Abstract, page 59, 3rd line from bottom.

Column 9, line 5: In Figure (VIII), "R" at the far
   left of the figure, should read: -- HO --.
   Page 12, Figure (VIII).

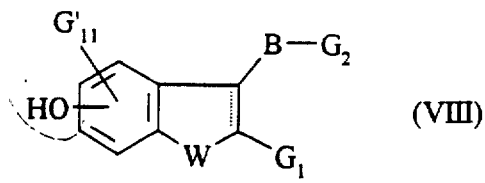

Column 10, line 43: "as defined formula (I)" should
   read: -- as defined for formula (I) --.
   Page 14, line 24

Column 21, line 22(approx.):
        "Melting point: 102° C,
        <u>Elemental microanalysis:</u>".
These 2 lines should be deleted as they already
appear in the paragraph above. Page 30, lines 12
and 13.

Column 21, line 66: "obron" should read -- boron --.
   Page 31, line 8

Column 27, line 58: "Example b 1," should read:
   -- Example 1, --. Page 39, line 10

UNITED STATES PATENT AND TRADEMARK OFFICE
CERTIFICATE OF CORRECTION

PATENT NO. : 6,147,110
DATED : November 14, 2000                    Page 2 of 5
INVENTOR(S) : D. Lesieur, N. Ruiz, V. Wallez, S. Boye, C. Bennejean, P. Renard, P. Delagrange It is certified that error appears in the above-identified patent and that said Letters Patent is hereby corrected as shown below:

Column 28, line 36: "iodacetamide" should read: -- iodoacetamide --. Page 40, line 7

Column 28, line 63: "Benzyl-5-2-" should read: -- Benzyl-5-(2- --. Page 40, line 17

Column 31, line 29: "Examples 104 to" should read: -- Examples 103 to --. Page 44, line 1

Column 35, line 23(approx): "Tables" should read: -- Tablets --. Page 50, line 12

Column 36, line 7: At the beginning of the line, "having to 7" should read: -- having 5 to 7 --. Page 51, line 23

Column 36, line 33(approx): After "$R_{21}$," in the second formula ($G_{21}$), insert the word -- and --. Preliminary Amendment dtd 12/23/98, <u>Claim 1, line 9</u> on page 52.

Column 37, line 42: Delete "from" near the beginning of the line. Preliminary Amendment dtd 12/23/98, <u>Claim 1, line 29</u>, on page 53.

Column 37, line 42: Insert the word "from" between "selected" and "nitrogen,". Page 53, line 29

Column 37, line 49: "and/or" should read -- or --. Preliminary Amendment dtd 12/23/98, <u>Claim 1, line 5</u>, on page 53.

UNITED STATES PATENT AND TRADEMARK OFFICE
CERTIFICATE OF CORRECTION

PATENT NO. : 6,147,110
DATED : November 14, 2000
INVENTOR(S) : D. Lesieur, N. Ruiz, V. Wallez, S. Boye, C. Bennejean, P. Renard, P. Delagrange Page 3 of 5

It is certified that error appears in the above-identified patent and that said Letters Patent is hereby corrected as shown below:

Column 37, line 62: At the beginning of the line, "ceutically acceptable" should read: -- ceutically-acceptable --. Preliminary Amendment dtd 12/23/98, Claim 1, line 14 on page 54.

Column 38, line 27: At the beginning of the line, "represent" should read: -- represents --. Page 56, line 7

Column 38, Errors in Claim 15:
  line 33: Delete the comma after the word "structure";
  line 34: After "R'" insert a -- , (comma) --;
  line 35: After the word "alkyl" insert a -- , (comma) --;
  line 40: After the word "hydrogen" insert a -- , (comma) --;
  line 41: Delete the comma after the word "alkenyl";
  Preliminary Amendment dtd 12/23/98, lines 2,3,6,7 and 8 on page 56.

UNITED STATES PATENT AND TRADEMARK OFFICE
CERTIFICATE OF CORRECTION

PATENT NO. : 6,147,110
DATED : November 14, 2000            Page 4 of 5
INVENTOR(S) : D. Lesieur, N. Ruiz, V. Wallez, S. Boye, C. Bennejean, P. Renard, P. Delagrange It is certified that error appears in the above-identified patent and that said Letters Patent is hereby corrected as shown below:

```
Column 38, Errors in Claim 16:
    line 46:  After "G₁₁" delete the comma;
    line 47:  After the word "structure" delete the
    comma;
    line 52:  Insert a -- ,(comma) -- after
     "hydrogen";
    line 53:  Delete the comma after the word
    "alkenyl".
    Preliminary Amendment dtd 12/23/98, lines 2,3,6
    and 7 on page 56.

Column 38, Errors in Claim 17:
    line 56:  Delete the comma after "R" at the end
    of the line;
    line 57:  Delete the comma after "structure";
    line 58:  Insert a -- , (comma) -- after
    "R'"(first instance);
    line 59:  Insert a -- , (comma) -- after
    "-alkyl", page 57, line 3
    line 62:  Insert a -- , (comma) -- after
    "aryl";
    line 64:  Insert a -- , (comma) -- after
    "hydrogen";
    line 65:  Delete the comma after "alkenyl";
    Preliminary Amendment dtd 12/23/98, lines
    3,4,6,7, and 8, page 57
```

UNITED STATES PATENT AND TRADEMARK OFFICE
CERTIFICATE OF CORRECTION

PATENT NO. : 6,147,110
DATED : November 14, 2000                Page 5 of 5
INVENTOR(S) : D. Lesieur, N. Ruiz, V. Wallez, S. Boye, C. Bennejean, P. Renard, P. Delagrange It is certified that error appears in the above-identified patent and that said Letters Patent is hereby corrected as shown below:

Column 39, Errors in Claim 18:

line 3: Delete the comma after "$G_{11}$";
    line 4: Delete the comma after "structure";
    line 9: Insert a -- , (comma) -- after "hydrogen";
    line 10: Delete the comma after "alkenyl".
    Preliminary Amendment dtd 12/23/98, lines 2,3,6 and 8, page 57.

Column 40, line 3: "N-{(2-[5-" should read:
    -- N-{2-[5-(2- --. Page 57, line 25

Signed and Sealed this

Eighth Day of May, 2001

Attest:

NICHOLAS P. GODICI

*Attesting Officer*     *Acting Director of the United States Patent and Trademark Office*